US010568912B2

(12) United States Patent
Anversa et al.

(10) Patent No.: US 10,568,912 B2
(45) Date of Patent: Feb. 25, 2020

(54) TREATMENT OF HEART DISEASE

(71) Applicant: AAL Scientifics, Inc., New York, NY (US)

(72) Inventors: Piero Anversa, New York, NY (US); Annarosa Leri, New York, NY (US)

(73) Assignee: AAL Scientifics, Inc., New York, NY (US)

(*) Notice: Subject to any disclaimer, the term of this patent is extended or adjusted under 35 U.S.C. 154(b) by 31 days.

(21) Appl. No.: 15/804,339

(22) Filed: Nov. 6, 2017

(65) Prior Publication Data

US 2018/0055889 A1 Mar. 1, 2018

Related U.S. Application Data

(60) Continuation of application No. 15/135,774, filed on Apr. 22, 2016, now Pat. No. 9,808,489, which is a division of application No. 13/508,838, filed as application No. PCT/US2010/055993 on Nov. 9, 2010, now abandoned.

(60) Provisional application No. 61/259,351, filed on Nov. 9, 2009.

(51) Int. Cl.
*A61K 35/34* (2015.01)
*C12N 5/0775* (2010.01)
*C12N 5/077* (2010.01)
*A61K 35/12* (2015.01)

(52) U.S. Cl.
CPC ............ *A61K 35/34* (2013.01); *C12N 5/0657* (2013.01); *C12N 5/0662* (2013.01); *A61K 35/12* (2013.01); *C12N 2501/105* (2013.01)

(58) Field of Classification Search
None
See application file for complete search history.

(56) References Cited

U.S. PATENT DOCUMENTS

| | | | |
|---|---|---|---|
| 5,843,780 A | 12/1998 | Thomson | |
| 5,945,577 A | 8/1999 | Stice et al. | |
| 5,994,619 A | 11/1999 | Stice et al. | |
| 6,200,806 B1 | 3/2001 | Thomson | |
| 6,235,970 B1 | 5/2001 | Stice et al. | |
| 7,547,674 B2 | 6/2009 | Anversa et al. | |
| 7,875,451 B2 | 1/2011 | Murry et al. | |
| 8,425,928 B2 | 4/2013 | Martinson et al. | |
| 9,132,226 B2 | 9/2015 | Martinson et al. | |
| 9,534,204 B2 | 1/2017 | Anversa et al. | |
| 9,808,489 B2 | 11/2017 | Anversa et al. | |
| 2001/0013134 A1 | 8/2001 | Sarvetnick et al. | |
| 2004/0158289 A1 | 8/2004 | Girouard et al. | |
| 2005/0053588 A1 | 3/2005 | Yin | |
| 2005/0187607 A1 | 8/2005 | Akhtar et al. | |
| 2006/0177453 A1 | 8/2006 | Mather et al. | |
| 2006/0239983 A1 | 10/2006 | Anversa et al. | |
| 2007/0031434 A1 | 2/2007 | Aguet | |
| 2007/0116691 A1 | 5/2007 | Cambier et al. | |
| 2007/0134254 A1 | 6/2007 | Kinch et al. | |
| 2007/0166288 A1 | 7/2007 | Murry et al. | |
| 2008/0019944 A1 | 1/2008 | Terzic et al. | |
| 2008/0241067 A1 | 10/2008 | Zimmerman et al. | |
| 2008/0267921 A1 | 10/2008 | Marban et al. | |
| 2008/0292677 A1 | 11/2008 | Cortiella et al. | |
| 2009/0018061 A1 | 1/2009 | Williams et al. | |
| 2009/0148421 A1 | 6/2009 | Anversa et al. | |
| 2009/0162329 A1 | 6/2009 | Anversa et al. | |
| 2009/0180998 A1 | 7/2009 | Anversa et al. | |
| 2010/0143345 A1 | 6/2010 | Kinch et al. | |
| 2010/0260749 A1 | 10/2010 | Kinch et al. | |
| 2011/0091428 A1 | 4/2011 | Anversa et al. | |
| 2012/0128638 A1 | 5/2012 | Gaussin et al. | |
| 2012/0288481 A1 | 11/2012 | Anversa et al. | |
| 2012/0321595 A1 | 12/2012 | Anversa et al. | |
| 2013/0216508 A1 | 8/2013 | Anversa et al. | |
| 2016/0220614 A1 | 8/2016 | Anversa et al. | |
| 2017/0165301 A1 | 6/2017 | Anversa et al. | |
| 2017/0258853 A1 | 9/2017 | Anversa et al. | |

FOREIGN PATENT DOCUMENTS

| | | |
|---|---|---|
| EP | 1135153 B1 | 4/2005 |
| KR | 10-2009-0019078 A | 2/2009 |
| WO | WO 2005/026332 A1 | 3/2005 |
| WO | WO 2006/047638 A2 | 5/2006 |
| WO | WO 2006/052925 A2 | 5/2006 |
| WO | WO 2007/073499 A2 | 6/2007 |
| WO | WO 2007/124594 A1 | 11/2007 |
| WO | WO 2007/141309 A2 | 12/2007 |
| WO | WO 2007/149447 A2 | 12/2007 |
| WO | WO 2008/010101 A2 | 1/2008 |
| WO | WO 2009/008901 A2 | 1/2009 |
| WO | WO 2009/062143 A2 | 5/2009 |

(Continued)

OTHER PUBLICATIONS

"Late-Breaking Basic Science Abstracts From the American Heart Association's Scientific Sessions 2009, Orlando, Florida, Nov. 14-18, 2009", Circulation Research (2009); 105(12): e55-e62.
Anversa and Olivetti. "Cellular basis of physiological and pathological myocardial growth." In: Handbook of Physiology, Section 2, The Heart. (2011); (eds. Page, et al., New York Oxford University Press, pp. 75-144.
Arda, H. Efsun, et al. "Gene regulatory networks governing pancreas development." Developmental Cell (2013); 25.1: 5-13.
Bader, Erik, et al. "Identification of proliferative and mature β-cells in the islets of Langerhans." Nature (2016); 535.7612: 430-434.
Baker et al., "Role of Insulin-like Growth Factors in Embryonic and Postnatal Growth." Cell (1993); 75:73-82.
Bearzi et al., "Human cardiac stem cells." PNAS (2007); 104(35):14068-14073.
Beltrami et al., "Adult Cardiac Stem Cells are Multipotent and Support Myocardial Regeneration." Cell (2003); 114:763-776.
Bender-Kim et al. "Identification of bronchioalveolar stem cells in normal lung and lung cancer." Cell (2005); 121(6): 823-835.
Blaauw et al., "Stretch-induced hypertrophy of isolated adult rabbit cardiomyocytes." Am J Physiol Heart Circ Physiol (2010); 299:H780-H787.

(Continued)

Primary Examiner — David W Berke-Schlessel
(74) Attorney, Agent, or Firm — Troutman Sanders LLP

(57) ABSTRACT

Disclosed herein are methods, compositions and kits for treating cardiac stem cells to be administered to a subject in (Continued)

need thereof, e.g., with a damaged myocardium. The methods, composition and kits of the invention can be used to treat cardiovascular diseases such as heart failure, myocardial infarction and an age-related cardiomyopathy.

34 Claims, No Drawings

Specification includes a Sequence Listing.

(56) References Cited

FOREIGN PATENT DOCUMENTS

| WO | WO 2009/073518 A1 | 6/2009 |
|---|---|---|
| WO | WO 2011/057249 A2 | 5/2011 |
| WO | WO 2011/057251 A2 | 5/2011 |
| WO | WO 2012/047951 A2 | 4/2012 |
| WO | WO 2017/156076 A1 | 9/2017 |

OTHER PUBLICATIONS

Bonner-Weir, Susan, and Aguayo-Mazzicato, Christina. "Physiology: Pancreatic β-cell heterogeneity revisited." Nature (2016); 535.7612: 365-366.
Boudina, Sihem, et al. "Diabetic cardiomyopathy revisited." Circulation (2007); 115.25: 3213-3223.
Brown and Schneyer. "Emerging roles for the TGFβ family in pancreatic β-cell homeostasis." Trends Endocrinol Metab. (2010); 21(7): 441-448.
Buja and Vela, "Cardiomyocyte death and renewal in the normal and diseased heart." Cardiovascular Pathology (2008); 17.6: 349-374.
Cairns, Linda A., et al. "Kit regulatory elements required for expression in developing hematopoietic and germ cell lineages." Blood (2003); 102.12: 3954-3962.
Chimenti et al., "Senescence and Death of Primitive Cells and Myocytes Lead to Premature Cardiac Aging and Heart Failure." Circ Res. (2003); 93:604-613.
Christie et al., "The registry of the international society for heart and lung transplantation: twenty-sixth official adult lung and heart-lung transplantation report—2009." J Heart Lung Transplant (2009); 28:1031-1049.
Cortiella, et al. "Tissue-Engineered Lung: An In Vivo and In Vitro Comparison of Polyglycolic Acid and Pluronic F-127 Hydrogel/Somatic Lung Progenitor Cell Constructs to Support Tissue Growth." Tissue Engineering (2006); 12: 1213-1225.
De Gasperi, Rita, et al. "The IRG mouse: A two-color fluorescent reporter for assessing Cre-mediated recombination and imaging complex cellular relationships in situ." Genesis (2008); 46.6: 308-317.
Dirice, Ercument, et al. "Soluble factors secreted by T cells promote β-cell proliferation." Diabetes (2014); 63.1: 188-202.
Dor, Yuval, and Glaser, Benjamin. "(β-cell dedifferentiation and type 2 diabetes." New England Journal of Medicine (2013); 368.6: 572-573.
Dor, Yuval, et al. "Adult pancreatic β-cells are formed by self-duplication rather than stem-cell differentiation." Nature (2004); 429.6987: 41-46.
Dorrell, Craig, et al. "Human islets contain four distinct subtypes of [beta] cells." Nature Communications (2016); 7: 11756.
Ellison, Georgina M., et al. "Adult c-kit pos cardiac stem cells are necessary and sufficient for functional cardiac regeneration and repair." Cell (2013); 154.4: 827-842.
Erbay et al., "IGF-11 transcription in skeletal myogenesis is controlled by mTOR and nutrients." The Journal of Cell Biology (2003); 163(5):931-936.
Esposito, Irene, et al. "The stem cell factor-c-kit system and mast cells in human pancreatic cancer." Laboratory Investigation (2002); 82.11: 1481-1492.
Extended European Search Report in European Patent Application No. 10829273.1 dated Oct. 2, 2013, 9 pages.
Extended European Search Report in European Patent Application No. 10829275.6 dated Nov. 26, 2013, 7 pages.
Extended European Search Report in European Patent Application No. 11831492.1 dated Mar. 7, 2014, 6 pages.
Feng, Zhi-Chao, et al. "A survival kit for pancreatic beta cells: stem cell factor and c-Kit receptor tyrosine kinase." Diabetologia (2015); 58.4: 654-665.
Ferreira-Martins, João, et al. "Cardiomyogenesis in the Developing Heart Is Regulated by C-Kit-Positive Cardiac Stem Cells." Circulation Research (2012); 110.5: 701-715.
Geiss, Gary K., et al. "Direct multiplexed measurement of gene expression with color-coded probe pairs." Nature Biotechnology (2008); 26.3: 317-325.
Geissler, Edwin N., et al. "The dominant-white spotting (W) locus of the mouse encodes the c-kit proto-oncogene." Cell (1988); 55.1: 185-192.
Gomez, Danielle L., et al. "Neurogenin 3 expressing cells in the human exocrine pancreas have the capacity for endocrine cell fate." PLOS One (2015); 10.8: e0133862.
Gong, JiaQing, et al. "Islet-derived stem cells from adult rats participate in the repair of islet damage." Journal of Molecular Histology (2012); 43.6: 745-750.
Gonzalez et al., "Activation of Cardiac Progenitor Cells Reverses the Failing Heart Senescent Phenotype and Prolongs Lifespan." Circ Res. (2008); 102:597-606.
Goodell, Margaret A., et al. "Somatic stem cell heterogeneity: diversity in the blood, skin and intestinal stem cell compartments." Nature Reviews Molecular Cell Biology (2015); 16.5: 299-309.
Goss, Garrett M., et al. "Differentiation potential of individual olfactory c-Kit+ progenitors determined via multicolor lineage tracing." Developmental Neurobiology (2016); 76.3: 241-251.
Gradwohl, Gérard, et al. "Neurogenin3 is required for the development of the four endocrine cell lineages of the pancreas." Proceedings of the National Academy of Sciences (2000); 97.4: 1607-1611.
Gu, Guoqiang, et al. "Direct evidence for the pancreatic lineage: NGN3+ cells are islet progenitors and are distinct from duct progenitors." Development (2002); 129.10: 2447-2457.
Hadi, Hadi A.R., and Suwaidi, Jassim Ai. "Endothelial dysfunction in diabetes mellitus." Vascular Health and Risk Management (2007); 3.6: 853-876.
Hare et al., "A Randomized, Double-Blind, Placebo-Controlled, Dose-Escalation Study of Intravenous Adult Human Mesenchymal Stem Cells (Prochymal) After Acute Myocardial Infarction." Journal of the American College of Cardiology (2009); 54(24): 2277-2286.
Hatzistergos, Konstantinos E., et al. "cKit+ cardiac progenitors of neural crest origin." Proceedings of the National Academy of Sciences (2015); 112.42: 13051-13056.
Heger, Klaus, et al. "CreERT2 expression from within the c-Kit gene locus allows efficient inducible gene targeting in and ablation of mast cells." European Journal of Immunology (2014); 44.1: 296-306.
Himanen, Juha P., et al. "Ligand recognition by A-class Eph receptors: crystal structures of the EphA2 ligand-binding domain and the EphA2/ephrin-A1 complex." EMBO Reports (2009); 10.7: 722-728.
Hosoda, Toru, et al. "Clonality of mouse and human cardiomyogenesis in vivo." Proceedings of the National Academy of Sciences (2009); 106.40: 17169-17174.
Hsu, Ya-Chieh, and Fuchs, Elaine. "A family business: stem cell progeny join the niche to regulate homeostasis." Nature Reviews Molecular Cell Biology (2012); 13.2: 103-114.
Hu et al., "An analysis of the effects of stretch on IGF-1 secretion from rat ventricular fibroblasts." Am J Physiol Heart Circ Physiol (2007); 293:H677-H683.
Hua, Jinlian, et al. "Characterization of mesenchymal stem cells (MSCs) from human fetal lung: potential differentiation of germ cells." Tissue and Cell (2009); 41.6: 448-455.
Hua, Xiu-feng, et al. "Pancreatic insulin-producing cells differentiated from human embryonic stem cells correct hyperglycemia in SCID/NOD mice, an animal model of diabetes." PLOS One (2014); 9.7: e102198.

(56) References Cited

OTHER PUBLICATIONS

International Search Report and Written Opinion in International Application No. PCT/US2010/055993 dated Aug. 2, 2011, 10 pages.
International Preliminary Report on Patentability in International Patent Application No. PCT/US2010/055993 dated May 15, 2012, 6 pages.
International Search Report and Written Opinion in International Application No. PCT/US2010/055999 dated Aug. 2, 2011, 10 pages.
International Preliminary Report on Patentability in International Application No. PCT/US2010/055999 dated May 15, 2012, 6 pages.
International Search Report and Written Opinion in International Application No. PCT/US2011/054849 dated Apr. 26, 2012, 11 pages.
International Preliminary Report on Patentability in International Application No. PCT/US2011/054849 dated Apr. 9, 2013, 7 pages.
International Search Report and Written Opinion in International Application No. PCT/US2017/021290 dated Jun. 7, 2017, 15 pages.
Ishkitiev et al., "Pancreatic differentiation of human dental pulp CD117+ stem cells." Regen. Med. (2013); 8(5): 597-612.
Itzhaki-Alfia et al., "Patient Characteristics and Cell Source Determine the Number of Isolated Human Cardiac Progenitor Cells." Circulation (2009); 120:2559-2566.
Jennings, Rachel E., et al. "Human pancreas development." Development (2015); 142.18: 3126-3137.
Jiang and Morahan. "Pancreatic stem cells: from possible to probable." Stem Cell Reviews and Reports (2012); 8.3: 647-657.
Kajstura et al., "Evidence for human lung stem cells." N Engl J Med, 364(19): 1795-1806 (2011).
Kajstura et al., "IGF-1 Overexpression Inhibits the Development of Diabetic Cardiomyopathy and Angiotensin 11-Mediated Oxidative Stress." Diabetes (2001), 50:1414-1424.
Kawamoto et al., "CD34-Positive Cells Exhibit Increased Potency and Safety for Therapeutic Neovascularization After Myocardial Infarction Compared With Total Mononuclear Cells." Circulation (2006); 114:2163-2169.
Keenan, Hillary A., et al. "Residual insulin production and pancreatic β-cell turnover after 50 years of diabetes: Joslin Medalist Study." Diabetes (2010); 59.11: 2846-2853.
Kikawa et al., "Regulation of the EphA2 kinase by the low molecular weight tyrosine phospatase induces transformation." J. Biol. Chem. (2002); 277(42): 39274-39279.
Klein, Sabine, et al. "Interstitial cells of Cajal integrate excitatory and inhibitory neurotransmission with intestinal slow-wave activity." Nature Communications (2013); 4: 1630.
Kollet et al., "HGF, SDF-1, and MMP-9 are involved in stress-induced human CD34+ stem cell recruitment to the liver." The Journal of Clinical Investigation (2003); 112(2):160-169.
Kotton et al. "Lung stem cells." Cell Tissue Res (2008); 331(1):145-156.
Kotton et al., "Lung stem cells: new paradigms." Experimental Hematology (2004); 32(4): 340-343.
Kretzschmar and Watt. "Lineage tracing." Cell (2012); 148.1: 33-45.
Krishnamurthy, Mansa, et al. "c-Kit in Early Onset of Diabetes: A Morphological and Functional Analysis of Pancreatic β-Cells in c-Kit Wv Mutant Mice." Endocrinology (2007); 148.11: 5520-5530.
Kroon, Evert, et al. "Pancreatic endoderm derived from human embryonic stem cells generates glucose-responsive insulin-secreting cells in vivo." Nature Biotechnology (2008); 26.4: 443-452.
Le Roith, "Regulation of proliferation and apoptosis by the insulin-like growth factor I receptor." Growth Hormone & IGF Research (2000); Supplement A:S12-S13.
Lemper, Marie, et al. "Reprogramming of human pancreatic exocrine cells to β-like cells." Cell Death & Differentiation (2015); 22.7: 1117-1130.
Leri et al., "Cardiac Stem Cells and Mechanisms of Myocardial Regeneration." Physiol Rev (2005); 85:1373-1416.
Leri, Annarosa, and Anversa, Piero. "Complexity of Tracking the Fate of Adult Progenitor Cells." Circulation Research (2016); 119.10: 1067-1070.
Leri, Annarosa, et al. "Origin of cardiomyocytes in the adult heart." Circulation Research (2015); 116.1: 150-166.
Linke et al., "Stem cells in the dog heart are self-renewing, clonogenic, and multipotent and regenerate infarcted myocardium, improving cardiac function." PNAS (2005); 102(25):8966-8971.
Liu, Qiaozhen, et al. "c-kit+ cells adopt vascular endothelial but not epithelial cell fates during lung maintenance and repair." Nature Medicine (2015); 21.8: 866-868.
Liu, Xiaoli, et al. "Rescue of neonatal cardiac dysfunction in mice by administration of cardiac progenitor cells in utero." Nature Communications (2015); 6: 8825.
Losordo et al., "Intramyocardial Transplantation of Autologous CD34+ Stem Cells for Intractable Angina: A Phase Iiiia Double-Blind, Randomized Controlled Trial." Circulation (2007); 115:3165-3172.
Lu, Jingwei, et al. "A novel technology for hematopoietic stem cell expansion using combination of nanofiber and growth factors." Recent Patents on Nanotechnology (2010); 4.2: 125-134.
Lusis et al., "Isolation of clonogenic, long-term self renewing embryonic renal stem cells." Stem Cell Research (2010); 5(1): 23-39.
Ma, Fengxia, et al. "Isolation of Pancreatic Progenitor Cells with the Surface Marker of Hematopoietic Stem Cells." International Journal of Endocrinology (2012); vol. 2012, Article ID 948683, 8 pages.
Maeng et al., "Endothelial progenitor cell homing: prominent role of the IGF2-IGF2R-PLC beta2 axis." Blood (2009); 113:233-243.
Manoranjan, Branavan, et al. "Foxg1 interacts with bmi1 to regulate self-renewal and tumorigenicity of medulloblastoma stem cells." Stem Cells (2013); 31.7: 1266-1277.
McBride, Jennifer L., and Ruiz, Joseph C. "Ephrin-A1 is expressed at sites of vascular development in the mouse." Mechanisms of Development (1998); 77.2: 201-204.
McDevitt et al., "Proliferation of cardiomyocytes derived from human embryonic stem cells is mediated via the IGF/PI 3-kinase/Akt signaling pathway." Journal of Molecular and Cellular Cardiology (2005); 39:865-873.
McDonald, J.H. Handbook of Biological Studies (Sparky House Publishing, Baltimore, Maryland). No-Book, no page #.
Menge, Bjoern A., et al. "Long-term recovery of β-cell function after partial pancreatectomy in humans." Metabolism (2012); 61.5: 620-624.
Mezza, Teresa, and Kulkarni, Rohit N. "The regulation of pre-and post-maturational plasticity of mammalian islet cell mass." Diabetologia (2014); 57.7: 1291-1303.
Miao et al., "Activation of EphA2 kinase suppresses integrin function and causes focal-adhesion-kinase dephosphorylation", Nature Cell Biology (2000); 2: 62-69.
Murasawa et al., "Niche-Dependent Translineage Commitment of Endothelial Progenitor Cells, Not Cell Fusion in General, Into Myocardial Lineage Cells." Arterioscler Thromb Vasc Biol. (2005); 25:1388-1394.
Murtaugh and Melton. "Genes, signals, and lineages in pancreas development." Annual Review of Cell and Developmental Biology (2003); 19.1: 71-89.
Muzumdar, Mandar Deepak, et al. "A global double-fluorescent Cre reporter mouse." Genesis (2007); 45.9: 593-605.
Nadal-Ginard, Bernardo, et al. "Absence of Evidence Is Not Evidence of Absence Pitfalls of Cre Knock-Ins in the c-Kit Locus." Circulation Research (2014); 115.4: 415-418.
Ogita, Hisakazu, et al. "EphA4-mediated Rho activation via Vsm-RhoGEF expressed specifically in vascular smooth muscle cells." Circulation Research (2003); 93.1: 23-31.
Oram, Richard A., et al. "The majority of patients with long-duration type 1 diabetes are insulin microsecretors and have functioning beta cells." Diabetologia (2014); 57.1: 187-191.
Orioli et al., "The Eph receptor family: axonal guidance by contact repulsion", TIG (1997); 13(9): 354-359.
Orlic et al., "Bone marrow cells regenerate infarcted myocardium." Nature (2001); 410:701-705.

(56) References Cited

OTHER PUBLICATIONS

Orlic, D., et al. "Purification and characterization of heterogeneous pluripotent hematopoietic stem cell populations expressing high levels of c-kit receptor." Blood (1993); 82.3: 762-770.
Padin-Iruegas et al., "Cardiac Progenitor Cells and Biotinylated Insulin-Like Growth Factor-1 Nanofibers Improve Endogenous and Exogenous Myocardial Regeneration After Infarction." Circulation (2009); 120:876-887.
Pandey et al., "Activation of the Eck Receptor Protein Tyrosine Kinase Stimulates Phosphatidylinositol 3-Kinase Activity", The Journal of Biological Chemistry (1994); 269(48): 30154-30157.
Parri, Matteo, et al. "EphrinA1 activates a Src/focal adhesion kinase-mediated motility response leading to rho-dependent actino/myosin contractility." Journal of Biological Chemistry (2007); 282.27: 19619-19628.
Pasquale, E.B. "The Eph family of receptors", Current Opinion in Cell Biology (1997); 9: 608-615.
Perl, S., et al. "Significant human β-cell turnover is limited to the first three decades of life as determined by in vivo thymidine analog incorporation and radiocarbon dating." The Journal of Clinical Endocrinology & Metabolism 95.10 (2010): E234-E239.
Peters, Katharina, et al. "Expression of stem cell markers and transcription factors during the remodeling of the rat pancreas after duct ligation." Virchows Archiv (2005); 446.1: 56-63.
Petley et al., "Variation Among Cell Types in the Signaling Pathways by which IGF-1 Stimulates Specific Cellular Responses." Horm Metab Res (1999), 31:70-76.
Philippou et al., "Type I insulin-like growth factor receptor signaling in skeletal muscle regeneration and hypertrophy." J Musculoskelet Neuronal Interact (2007); 7(3):208-218.
Pratt et al., "Activation of the EphA2 tyrosine kinase stimulates the MAP/ERK kinase signaling cascade", Oncogene (2002); 21: 7690-7699, 2002.
Quesada et al., "Physiology of the pancreatic α-cell and glucagon secretion: role in glucose homeostasis and diabetes." Journal of Endocrinology (2008); 199: 5-19.
Quesenberry, Peter J., et al. "Perspective: fundamental and clinical concepts on stem cell homing and engraftment: a journey to niches and beyond." Experimental Hematology (2005); 33.1: 9-19.
Qu, Xiaoling, et al. "Notch-mediated post-translational control of Ngn3 protein stability regulates pancreatic patterning and cell fate commitment." Developmental Biology (2013); 376.1: 1-12.
Rosen et al., "Specific, Temporally Regulated Expression of the Insulin-Like Growth Factor II Gene During Muscle Cell Differentiation." Endocrinology (1993); 133(2):474-481.
Rosenthal et al., "Regulation of Insulin-like Growth Factor (IGF) I Receptor Expression During Muscle Cell Differentiation." J. Clin. Invest. (1991), 87:1212-1219.
Rosu-Myles et al., "A unique population of bone marrow cells migrates to skeletal muscle via hepatocyte growth factor/c-met axis." Journal of Cell Science (2005); 118:4343-4352.
Rota et al., "Local Activation or Implantation of Cardiac Progenitor Cells Rescues Scarred Infarcted Myocardium Improving Cardiac Function." Circ Res. (2008); 103:107-116.
Rota, Marcello, et al. "Bone marrow cells adopt the cardiomyogenic fate in vivo." Proceedings of the National Academy of Sciences (2007); 104.45: 17783-17788.
Saisho, Yoshifumi. "Importance of beta cell function for the treatment of type 2 diabetes." Journal of Clinical Medicine (2014); 3.3: 923-943.
Sanada, Fumihiro, et al. "c-Kit-Positive Cardiac Stem Cells Nested in Hypoxic Niches Are Activated by Stem Cell Factor Reversing the Aging Myopathy." Circulation Research (2014); 114.1: 41-55.
Sandstedt et al., "C-kit+ CD45− cells found in the adult human heart represent a population of endothelial progenitor cells." Basic Res Cardiol (2010); 105(4):545-556.
Schächinger et al., "Intracoronary Bone Marrow—Derived Progenitor Cells in Acute Myocardial Infarction." The New England Journal of Medicine (2006); 355:1210-1221.

Seymour, Philip A. "Sox9: a master regulator of the pancreatic program." The Review of Diabetic Studies: RDS (2014); 11.1: 51-83.
Sherr, Jennifer L., et al. "Characterization of residual β cell function in long-standing type 1 diabetes." Diabetes/Metabolism Research and Reviews (2014); 30.2: 154-162.
Shih, Hung Ping, et al. "A Notch-dependent molecular circuitry initiates pancreatic endocrine and ductal cell differentiation." Development (2012); 139.14: 2488-2499.
Smith et al., "Regenerative Potential of Cardiosphere-Derived Cells Expanded From Percutaneous Endomyocardial Biopsy Specimens." Circulation (2007); 115:896-908.
Smukler, Simon R., et al. "The adult mouse and human pancreas contain rare multipotent stem cells that express insulin." Cell Stem Cell (2011); 8.3: 281-293.
Soyer, Josselin, et al. "Rfx6 is an Ngn3-dependent winged helix transcription factor required for pancreatic islet cell development." Development (2010); 137.2: 203-212.
Stephen, Lesley J., et al. "A critical role for the EphA3 receptor tyrosine kinase in heart development." Developmental Biology (2007); 302.1: 66-79.
Talhouk, Aline, et al. "Single-patient molecular testing with NanoString nCounter data using a reference-based strategy for batch effect correction." PLOS One (2016); 11.4: e0153844.
Ten Dijke, Peter, and Iwata, Kenneth K. "Growth factors for wound healing." Nature Biotechnology (1989); 7.8: 793-798.
Tiemann, Katharina, et al. "Expression of transcription factors and precursor cell markers during regeneration of β cells in pancreata of rats treated with streptozotocin." Virchows Archiv (2007); 450.3: 261-266.
Torella et al., "Cardiac Stem Cell and Myocyte Aging, Heart Failure, and Insulin-Like Growth Factor-1 Overexpression." Circulation Research (2004); 94:514-524.
Turner Anne M., et al., "Nonhematopoietic Tumor Cell Lines Express Stem Cell Factor and Display c-kit Receptors." Blood (1992); 80: 374-381.
Urbanek et al., "Cardiac Stem Cells Possess Growth Factor-Receptor Systems That After Activation Regenerate the Infarcted Myocardium, Improving Ventricular Function and Long-Term Survival." Circ Res. (2005); 97:663-673.
Urbanek et al., "Intense myocyte formation from cardiac stem cells in human cardiac hypertrophy." PNAS (2003); 100(18):10440-10445.
Urbanek et al., "Myocardial regeneration by activation of multipotent cardiac stem cells in ischemic heart failure." PNAS (2005), 102(24):8692-8697.
Urbanek et al., "Stem cell niches in the adult mouse heart." PNAS (2006); 103(24):9226-9231.
Van Berlo, Jop H., et al. "C-kit+ cells minimally contribute cardiomyocytes to the heart." Nature (2014); 509.7500: 337-341.
Veldman-Jones, Margaret H., et al. "Evaluating robustness and sensitivity of the NanoString technologies nCounter platform to enable multiplexed gene expression analysis of clinical samples." Cancer Research (2015); 75.13: 2587-2593.
Wajchenberg, Bernardo L. "Beta-cell failure in diabetes and preservation by clinical treatment." Endocrine Reviews (2007); 28.2: 187-218.
Weinberg, Noa, et al. "Lineage tracing evidence for in vitro dedifferentiation but rare proliferation of mouse pancreatic β-cells." Diabetes (2007); 56.5: 1299-1304.
Williams, Scott E., et al. "Asymmetric cell divisions promote Notch-dependent epidermal differentiation." Nature (2011); 470. 7334: 353-358.
Wilson et al., "Mechanisms of Signal Transduction: Control of MyoD Function during Initiation of Muscle Differentiation by an Autocrine Signaling Pathway Activated by Insulin-like Growth Factor-II." J. Biol. Chem. (2006); 281(40): 29962-29971.
Wu, Yuexiu, et al. "c-Kit and stem cell factor regulate PANC-1 cell differentiation into insulin- and glucagon-producing cells." Laboratory Investigation (2010); 90.9: 1373-1384.
Xiao, Xiangwei, et al. "No evidence for β cell neogenesis in murine adult pancreas." The Journal of Clinical Investigation (2013); 123.5: 2207-2217.

(56) References Cited

OTHER PUBLICATIONS

Xu, Xiaobo, et al. "β cells can be generated from endogenous progenitors in injured adult mouse pancreas." Cell (2008); 132.2: 197-207.

Yagihashi, Soroku, et al. "Dynamic pathology of islet endocrine cells in type 2 diabetes: β-Cell growth, death, regeneration and their clinical implications." Journal of Diabetes Investigation (2016); 7.2: 155-165.

Ye and D'Ercole, "Insulin-Like Growth Factor Actions During Development of Neural Stem Cells and Progenitors in the Central Nervous System." Journal of Neuroscience Research (2006); 83:1-6.

Zheng et al., "Proteomic Analysis for the Assessment of Different Lots of Fetal Bovine Serum as a Raw Material for Cell Culture. Part IV. Application of Proteomics to the Manufacture of Biological Drugs." Biotechnol. Prog. (2006); 22(5): 1294-1300.

Zhu et al., "IGFBP-4 is an inhibitor of canonical Wnt signalling required for cardiogenesis." Nature (2008); 454:345-349.

TREATMENT OF HEART DISEASE

CROSS-REFERENCE TO RELATED APPLICATIONS

This application is a continuation application of U.S. patent application Ser. No. 15/135,774, filed Apr. 22, 2016 and issued as U.S. Pat. No. 9,808,489, which is a divisional application of U.S. patent application Ser. No. 13/508,838, filed Aug. 29, 2012 (now abandoned), which is a 35 U.S.C. § 371 National Phase Entry of International Patent Application No. PCT/US2010/055993, filed Nov. 9, 2010, which designates the United States, and which claims benefit under 35 U.S.C. § 119(e) of U.S. Provisional Patent Application No. 61/259,351, filed Nov. 9, 2009. The contents of each application listed above are incorporated herein by reference in their entirety.

GOVERNMENT SUPPORT

This invention was made with Government support under Grant Numbers AG017042, AG037495, and HL092868 awarded by the National Institutes of Health. The Government has certain rights in the invention.

SEQUENCE LISTING

The contents of the text file submitted electronically herewith are incorporated herein by reference in their entirety: a computer readable format copy of the sequence listing (filename: AALS-002_03US_sequence_listing.txt, date recorded: Nov. 6, 2017, file size 23,185 bytes).

FIELD OF THE INVENTION

The invention relates generally to methods, compositions and kits for treatment of heart disease, and more particularly relates to methods, compositions and kits comprising cardiac stem cells for repairing a damaged heart tissue.

BACKGROUND OF THE INVENTION

Cardiovascular disease is a major health risk throughout the industrialized world. An estimated 81.1 million Americans suffer from one or more types of cardiovascular disease, including high blood pressure, coronary heart disease, heart failure, and stroke (Heart Disease and Stroke Statistics, American Heart Association, 2010). Cardiovascular disease is one of the leading causes of death in Americans.

Among cardiovascular diseases, ischemic heart disease is the most common cause of death in most western countries. Ischemic heart disease is characterized chronically by a healed infarct, foci of myocardial scarring, cavitary dilation, and impaired ventricular performance. One serious condition is myocardial infarction (MI), commonly known as a heart attack. Estimates for 2006 show that 8.5 million people in the United States suffer from MI (Heart Disease and Stroke Statistics, American Heart Association, 2010). MI is caused by a sudden and sustained lack of blood flow to an area of the heart, typically caused by narrowing of a coronary artery. Without adequate blood supply, the tissue becomes ischemic, leading to the death of myocytes and vascular structures. This area of necrotic tissue is referred to as the infarct site, the size of which determines survival, with the probability of recovery decreasing with increasing infarct size. For example, in humans, an infarct of 46% or more of the left ventricle triggers irreversible cardiogenic shock and death.

Although an ischemic injury can initiate a healing process, it leads to formation of a scar that does not possess the biochemical, physical and functional properties of the original myocardial tissue, and therefore, negatively affects the overall performance of the heart. These myocardial alterations can only be reversed by replacement of scarred tissue with functionally competent myocardium. Leri A et al, 85 Physiol Rev. 1373 (2005).

Previous studies have discussed that hematopoietic stem cells may improve the outcome of myocardial infarction in animal models (1-3). Bone marrow mononuclear cells, CD34-positive cells and mesenchymal stromal cells have been introduced clinically with rather consistent results. The intracoronary or intramyocardial injection of these cell classes has been shown to be safe and to produce a modest enhancement in systolic function (4-6). More recently, there is mounting evidence to suggest that the heart has regenerative potential in the event of myocardial injury. Recent studies have identified resident cardiac stem cells (CSCs) in the human heart (7, 8). Thus, regeneration of myocardial tissue after acute infarction has been attempted by employing CSCs. For example, implantation of growth factor-treated CSCs to the damaged myocardium or local activation of resident CSCs by intramyocardial administration of growth factors, e.g., insulin-like growth factor-1 (IGF-1) and hepatocyte growth factor (HGF), has been recently shown to have a possibility of recovering ventricular muscle mass in an in vivo model. Linke A et al., 102 PNAS 8966 (2005); Urbanek K et al., 97 Circ Res. 663 (2005); Rota M et al., 103 Circ Res. 107 (2008). However, regeneration of a functional myocadium by IGF-1 or HGF-treated CSCs is limited by CSC differentiation into mature and functionally competent myocytes.

The identification of resident cardiac stem cells in the human heart (7, 8), together with the isolation of a complex pool of cardiac cells, namely the cardiospheres (9), has implicated a potential implementation of these autologous cells for the management of the human disease. For example, preclinical studies have been completed and two phase 1 clinical trials in patients affected by acute (Identifier: NCT00893360) and chronic (Identifier: NCT00474461) ischemic cardiomyopathy are in progress. No information is currently available on the efficacy of human cardiac stem cells (hCSCs) in these pathological conditions. However, the age of the patient and the type and duration of the disease may affect the number and growth properties of these primitive cells. For instance, telomere attrition, cellular senescence and apoptosis all contribute to decrease the compartment of functionally-competent hCSCs in the old failing heart (10-12). Further, age and coronary artery disease may negatively affect the function of human cardiac stem cells (hCSCs) and their potential therapeutic efficacy for autologous cell transplantation in the failing heart. Accordingly, reconstitution of muscle mass by cell implantation after infarction is limited by two factors: number of cells engrafted into the recipient myocardium and modest differentiation of the cardiomyocyte progeny. As such, there is a strong need to develop methods to address the foregoing issues. Such methods would significantly improve stem cell-mediated treatment of heart diseases, e.g., myocardial infarctions, and provide new approaches to the management of human heart failure.

SUMMARY OF THE INVENTION

Aspects of the present invention stem from the discovery that human cardiac stem cells (hCSCs) expressing IGF-1 receptors (IGF-1R) and/or IGF-2 receptors (IGF-2R) show differential responses in growth reserve and differentiation after stimulation with IGF-1 or IGF-2. Further, it was discovered that while activation of IGF-2R-positive hCSCs with IGF-2 trigger apoptosis, activation of IGF-1R-positive hCSCs with IGF-2, for example, pre-treatment of hCSCs with IGF-2 prior to myocardial injection to an infarcted heart, enhances formation of mature myocytes and recovery of structure and function of the infracted heart in an in vivo rat model.

Accordingly, provided herein are methods, compositions and kits for treating cardiac stem cells to be administered to a subject in need thereof. Examples of the subject in need thereof include, but are not limited to, an individual diagnosed with or suffering from a damaged myocardium, myocardial infarction, a heart failure or an age-related cardiomyopathy. In one aspect, the method includes (a) contacting a population of cardiac stem cells with an effective amount of IGF-2 or a variant thereof; and (b) administering the population of cardiac stem cells from step (a) to the subject in need thereof. In one embodiment, the at least one cardiac stem cell generates a myocardial cell in the subject after administration.

In one embodiment, the population of cardiac stem cells is pre-selected for expression of IGF-1 receptor, e.g., ~100% of the population expresses the IGF-1 receptor. In further embodiment, the cardiac stem cells express both IGF-1 receptor and IGF-2 receptor. In another embodiment, the cardiac stem cells express IGF-1 receptor but no IGF-2 receptor.

In one embodiment, the effective amount of IGF-2 or a variant thereof is sufficient to increase expression of at least one marker for myocyte differentiation by at least about 10%, as compared to cardiac stem cells in the absence of IGF-2 or a variant thereof. Non-limiting examples of the marker for myocyte differentiation include α-sarcomeric actin, connexin-43, Nkx2.5, GATA-4 and MEF2C. In one embodiment, the effective amount of IGF-2 or a variant thereof is about 100 ng/mL.

The cardiac stem cells are contacted with IGF-2 or a variant thereof for an amount of time sufficient, to increase myocyte formation, or for the cardiac stem cells to confer acquisition of at least one adult cardiomyocyte phenotype, as compared to cardiac stem cells in the absence of IGF-2 or a variant thereof. Examples of adult cardiomyocyte phenotype include, but are not limited to, a myocyte volume greater than 2000 $\mu m^3$, contractility in response to electric stimulation, an elongated morphology, calcium tolerance, expression of contractile proteins (e.g., α-sarcomeric actin, myosin heavy chain, myosin light chains and tropomyosin), and activation of ionic current channels.

After contacting the population of cardiac stem cells with IGF-2 or a variant thereof, for a pre-defined amount of time, e.g., about 2 hours, the cardiac stem cells are administered to a subject in need thereof, e.g., by injection, or a catheter. In one embodiment, the cardiac stem cells are administered to an area of a damaged heart tissue of the subject, e.g., by an intramyocardial or intracoronary route.

In various embodiments, the cardiac stem cells can be isolated from a myocardial tissue of a subject.

In certain embodiments, the method described herein further comprises contacting a population of cardiac stem cells with IGF-1 prior to contact with IGF-2. Accordingly, another aspect of the invention provides a method of treating cardiac stem cells to be administered to a subject in need thereof, the method comprising (a) contacting a population of cardiac stem cells with an effective amount of IGF-1 or a variant thereof (b) contacting the population of cardiac stem cells from step (a) with an effective amount of IGF-2 or a variant thereof; and (c) administering the population of cardiac stem cells from step (b) to the subject in need thereof. In one embodiment, the at least one cardiac stem cell generates a myocardial cell in the subject after administration.

In one embodiment, the effective amount of IGF-1 or a variant thereof is sufficient to increase proliferation of the cardiac stem cells by at least about 10%, as compared to cardiac stem cells in the absence of IGF-1 or a variant thereof. In one embodiment, the effective amount of IGF-1 or a variant thereof is about 100 ng/mL.

In one embodiment, the cardiac stem cells are contacted with IGF-1 for at least about 12 hours.

A further aspect of the invention provides a composition that comprises at least one cardiac stem cell and an effective amount of IGF-2 or a variant thereof. In one embodiment, the composition further comprises a pharmaceutically acceptable carrier. In another embodiment, the composition further comprises a cell culture medium.

In one embodiment, at least one cardiac stem cell of the composition described herein expresses IGF-1 receptor. In further embodiment, the cardiac stem cell expresses both IGF-1 receptor and IGF-2 receptor. In another embodiment, the cardiac stem cell expresses IGF-1 receptor but no IGF-2 receptor.

In some embodiments, the composition described herein comprises an amount of IGF-2 or a variant thereof effective to increase expression of at least one marker for myocyte differentiation by at least about 10%, as compared to cardiac stem cells in the absence of IGF-2 or a variant thereof. Non-limiting examples of the marker for myocyte differentiation include α-sarcomeric actin, connexin-43, Nkx2.5, GATA-4 and MEF2C. In one embodiment, the composition of the invention comprises about 100 ng/mL of IGF-2 or a variant thereof.

The composition disclosed herein is administered to a subject in need thereof. Examples of the subject in need thereof include, but are not limited to, an individual diagnosed with or suffering from a damaged myocardium, a myocardial infarction, a heart failure or an age-related cardiomyopathy. In various embodiments, the subject in need thereof is a mammal, e.g., a human.

In some embodiments, the composition disclosed herein is administered to an area of a damaged heart tissue of the subject. Exemplary methods of administering cardiac stem cells to the subject include, but are not limited to, injection or delivery by a catheter. In some embodiments, cardiac stem cells are administered via an intramyocardial or intracoronary route.

In certain embodiments, the composition described herein further comprises an effective amount of IGF-1 or a variant thereof, wherein the effective amount of IGF-1 or a variant thereof is sufficient to increase proliferation of the cardiac stem cells by at least about 10%, as compared to cardiac stem cells in the absence of IGF-1 or a variant thereof. Accordingly, a yet further aspect of the invention provides a composition that comprises at least one cardiac stem cell and an effective amount of IGF-1 and IGF-2, and variants thereof. In one embodiment, IGF-2 or a variant thereof is added into the composition after the cardiac stem cell has been contacted with IGF-1.

Kits useful in carrying out the methods described herein also are provided. Such kits comprise at least one cardiac stem cell and an effective amount of IGF-2 or a variant thereof. In one embodiment, the kit disclosed herein further comprises IGF-1 or a variant thereof. In certain embodiment, the kit of the invention comprises a composition of the invention. In various embodiments, the kit can optionally contain instructions for using the kit to carry out the methods described herein. In some embodiments, the kit of the invention further comprises at least one syringe, one container and/or one catheter.

DETAILED DESCRIPTION OF THE INVENTION

Ischemic heart disease is a disease characterized by ischemia (reduced blood flow) to the heart tissue, usually due to coronary artery disease. One of the serious conditions is myocardial infarction (MI), commonly known as a heart attack. Due to an inadequate blood supply, the heart tissue becomes necrotic, which is known as an infarct. The size of the infarct negatively affects an individual's survival or recovery probability. There have been a few attempts to regenerate the necrotic tissue by transplanting cardiac stem cells to an area of a damaged myocardium. However, the number of autologous cardiac stem cells and/or their differentiation to mature cardiomyocytes is limited in an aging or failing heart. Thus, stem cell therapy for restoration of a damaged myocardium to its original condition has not yet been identified.

In accordance with aspects of the invention, the presence of different IGF-receptor systems, namely IGF-1R and IGF-2R, has been documented in cardiac stem cells, which in turn generates different human cardiac stem cell subsets with differential growth reserve. The inventors have demonstrated that pre-treatment of IGF-2R-positive cardiac stem cells with IGF-2 induces apoptosis, but pre-treatment of IGF-1R-positive cardiac stem cells with IGF-2, prior to injection into infarcted mice, promotes hCSC differentiation into mature myocytes and thus enhances myocardium regeneration. While IGF-2 favors hCSC commitment and acquisition of the cardiomyocyte phenotype, IGF-1 promotes hCSC proliferation. Accordingly, the inventors have shown that pre-treatment of hCSCs with IGF-1 followed by IGF-2 activates hCSCs, and promotes cell differentiation and myocardium regeneration.

Accordingly, some embodiments of the invention are generally related to methods, compositions and kits for treating cardiac stem cells to be administered to a subject in need thereof, e.g., an individual diagnosed with or suffering from a damaged myocardium. Another aspect of the invention relates to methods, compositions and kits for enhancing expansion and/or differentiation of cardiac stem cells to be administered to a subject in need thereof. A further aspect of the invention is directed to methods, compositions and kits for therapeutic treatment of cardiovascular diseases, e.g., myocardial infarction, heart failure or an age-related cardiomyopathy.

One aspect of the invention provides a method for treating cardiac stem cells to be administered to a subject in need thereof. The method includes (a) contacting a population of cardiac stem cells with an effective amount of IGF-2 or a variant thereof; and (b) administering the population of cardiac stem cells from step (a) to the subject in need thereof. In one embodiment, at least one cardiac stem cell generates a myocardial cell in the subject after the administration.

As used herein, the term "contacting" refers to any suitable means for delivering, or exposing, an agent to at least one cell. Exemplary delivery methods include, but are not limited to, direct delivery to cell culture medium, delivery to an in vitro scaffold in which cells are seeded, e.g., via perfusion or injection, or other delivery method well known to one skilled in the art. In one embodiment, IGF-2 or a variant thereof is added to the cell culture medium in which cardiac stem cells are cultured. In another embodiment, IGF-2 or a variant thereof is coated on a solid support on which the cardiac stem cells are attached. In still another embodiment, IGF-2 or a variant thereof is injected into a biocompatible gel (e.g., peptide gel, hydrogel) in which cardiac stem cells are encapsulated. In one embodiment, a population of cardiac stem cells is contacted with IGF-2 or a variant thereof added to the cell culture medium. The term "treatment" or "treated" as used herein, with respect to exposing cells to an agent, e.g., treatment of cardiac stem cells with IGF-2, is used herein interchangeably with the term "contacting".

The cardiac stem cells can be contacted with IGF-2 for any period of time, e.g., minutes, hours, or days. In some embodiments, the population of cardiac stem cells described herein are contacted with IGF-2 or a variant thereof for about 1 hour to 3 hours, for about 3 hours to about 6 hours, for about 6 hours to about 12 hours, for about 12 hours to about 1 day, for about 2 days to about 1 week, for about 1 week to about 1 month. In one embodiment, the cardiac stem cells are contacted with IGF-2 or a variant thereof for about 2 hours. In some embodiments, the cardiac stem cells can be contacted with IGF-2 or a variant thereof for at least about 15 minutes, at least about 30 minutes, at least about 1 hour, at least about 2 hours, at least about 3 hours, or at least about 6 hours.

In one embodiment, the cardiac stem cells are contacted with IGF-2 for an amount of time sufficient to increase myocyte formation, as compared to cardiac stem cells in the absence of IGF-2. The formation of myocytes can be detected by examining the morphological change of the treated CSCs from a round shape to an elongated shape with striations.

In another embodiment, the cardiac stem cells are contacted with IGF-2 for an amount of time sufficient for the cardiac stem cells to confer acquisition of at least one adult cardiomyocyte phenotype, as compared to cardiac stem cells in the absence of IGF-2. The adult cardiomyocyte phenotypes include, but are not limited to, a myocyte volume greater than 2000 µm³, contractility in response to electric stimulation, an elongated morphology, calcium tolerance, expression of contractile proteins, such as α-sarcomeric actin, myosin heavy chains, myosin light chains and tropomyosin, and activation of ion current channels, such as calcium ion channels. Methods for determining adult cardiomyocyte phenotypes have been well established in the art, e.g., see methods used in the Examples of U.S. Pat. No. 7,547,674 and U.S. Pat. App. Pub. Nos.: US 2009/0148421, US 2009/0180998, and US 2009/0162329, the contents of which are incorporated herein by reference in their entirety. Procedures for determining mechanical properties, e.g., contractility, of the adult cardiomyocytes have been previously described in Kanj et al., 68 Cancer 1910 (1991). A skilled artisan will be well aware of detecting expression of contractile proteins by western blot for protein levels or by qRT-PCR for mRNA levels. The electrophysiological measurement of ion channels in vitro can be performed by patch-clamp recording techniques well known to one of skill in the art.

In some embodiments, the population of cardiac stem cells described herein can be contacted more than once with IGF-2 or a variant thereof. In some embodiments, the cardiac stem cells can be contacted with IGF-2 and/or variants thereof at least twice, at least three times, at least four times, or at least five times. A different IGF-2 variant or a combination thereof can be used in each cell treatment.

In some embodiments, the cardiac stem cells can be contacted with at least one additional cytokine prior to administration, such as hepatocyte growth factor (HGF), insulin-like growth factor-1 (IGF-1), or a variant thereof. In one embodiment, cardiac stem cells are contacted with at least one additional cytokine prior to contacting with IGF-2 or a variant thereof. In alternative embodiment, cardiac stem cells are contacted with at least one additional cytokine after treatment with IGF-2 or a variant thereof. In such embodiments, the IGF-2-treated cardiac stem cells can be contacted with the additional cytokine prior to administration to a subject in need thereof.

In one embodiment, the cardiac stem cells are optionally contacted with hepatocyte growth factor (HGF) and/or insulin-like growth factor-1 (IGF-1). In such an embodiment, HGF can be present in an amount of about 0.1 ng/ml to about 400 ng/ml. In another embodiment, HGF can be present in an amount of about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml or about 400 ng/ml. In some embodiments, HGF can be present in an amount of at least about 25 ng/ml, at least about 100 ng/mL or at least about 200 ng/mL. In another embodiment, IGF-1 can be present in an amount of about 0.1 ng/ml to about 500 ng/ml. In a yet further embodiment, IGF-1 can be present in an amount of about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, or about 500 ng/ml. In some embodiments, IGF-1 can be present in an amount of at least about 25 ng/ml, at least about 100 ng/mL or at least about 200 ng/mL. HGF positively influences stem cell migration and homing through the activation of the c-Met receptor (Kollet et al. (2003) J. Clin. Invest. 112: 160-169; Linke et al. (2005) Proc. Natl. Acad. Sci. USA 102: 8966-8971; Rosu-Myles et al. (2005) J. Cell. Sci. 118: 4343-4352; Urbanek et al. (2005) Circ. Res. 97: 663-673). Similarly, IGF-1 and its corresponding receptor (IGF-1R) induce cardiac stem cell division, upregulate telomerase activity, hinder replicative senescence and preserve the pool of functionally-competent cardiac stem cells in the heart (Kajstura et al. (2001) Diabetes 50: 1414-1424; Torella et al. (2004) Circ. Res. 94: 514-524; Davis et al. (2006) Proc. Natl. Acad. Sci. USA 103: 8155-8160).

Some other non-limiting examples of cytokines that can be used to optionally treat cardiac stem cells prior to administration include Activin A, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Insulin-like Growth Factor-2, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-1, Thrombopoietin, Transforming Growth Factor-α, Transforming Growth Factor-β1, Transforming Growth Factor-β2, Transforming Growth Factor-β3, Vascular Endothelial Growth Factor, Wnt1, Wnt3a, and Wnt5a, and variants thereof, as described in Kanemura et al. (2005) Cell Transplant. 14:673-682; Kaplan et al. (2005) Nature 438:750-751; Xu et al. (2005) Methods Mol. Med. 121:189-202; Quinn et al. (2005) Methods Mol. Med. 121:125-148; Almeida et al. (2005) J Biol. Chem. 280: 41342-41351; Bamabe-Heider et al (2005) Neuron 48:253-265; Madlambayan et al. (2005) Exp Hematol 33: 1229-1239; Kamanga-Sollo et al. (2005) Exp Cell Res 311:167-176; Heese et al. (2005) Neuro-oncol. 7:476-484; He et al. (2005) Am J. Physiol. 289:H968-H972; Beattie et al. (2005) Stem Cells 23:489-495; Sekiya et al. (2005) Cell Tissue Res 320:269-276; Weidt (2004) Stem Cells 22:890-896; Encabo et al (2004) Stem Cells 22:725-740; and Buytaeri-Hoefen et al. (2004) Stem Cells 22:669-674, the entire text of each of which is incorporated herein by reference.

In another aspect of the invention, the cardiac stem cells are contacted with IGF-1 prior to IGF-2. Accordingly, a method of treating cardiac stem cells to be administered to a subject in need thereof, which involves IGF-1 and IGF-2, is also provided herein. The method includes (a) contacting a population of cardiac stem cells with an effective amount of IGF-1; (b) contacting the population of cardiac stem cells from step (a) with an effective amount of IGF-2; and (c) administering the population of cardiac stem cells from step (b) to the subject in need thereof. In one embodiment, the at least one cardiac stem cell generates a myocardial cell in the subject after the administration.

The cardiac stem cells can be contacted with IGF-1 for any period of time, e.g., minutes, hours, or days. In some embodiments, the cardiac stem cells can be contacted with IGF-1 until a desirable cell density is reached, e.g., about 40% confluency, about 50% confluency, about 60% confluency, about 70% confluency, about 80% confluency, about 90% confluency, or about 95% confluency. In some embodiments, the cardiac stem cells can be contacted with IGF-1 until the cell density is reached at a confluency of at least about 10%, at least about 20%, at least about 30% or at least about 40%. In one embodiment, the cardiac stem cells are contacted with IGF-1 as long as the cell confluency is less than about 80%, less than about 70%, less than about 60% or less than about 50%. The term "confluency" used herein refers to a measure of the number of the cells in a cell culture apparatus, e.g., a dish or a flask, and refers to the coverage of the dish or the flask by the cells. For example, 100% confluency means the dish is completely covered by the cells and there is no more room left for the cells to grow, whereas 50% confluency means roughly half of the dish is covered and there is room for cells to grow. One of skill in the art can determine cell confluency by examining the cell culture under a light microscope. In some embodiments, once the cardiac stem cells reach a certain confluency, e.g., about 50% to about 70%, a skilled artisan can passage the cells into multiple cell culture containers for further expansion of CSC in the presence of IGF-1 or a variant thereof. In some embodiments, the population of cardiac stem cells described herein are contacted with IGF-1 or a variant thereof for at least about 6 hours, at least about 7 hours, at least about 8 hours, at least about 9 hours, at least about 10 hours, at least about 11 hours, at least about 12 hours, at least about 1 day, at least about 2 days, at least about 1 week, at least about 2 weeks, or at least about 1 month. In one embodiment, the cardiac stem cells are contacted with IGF-1 thereof for at least about 12 hours.

In some embodiments, the population of cardiac stem cells described herein can be contacted more than once with IGF-1 or a variant thereof. In some embodiments, the cardiac stem cells can be contacted with IGF-1 and/or variants thereof at least twice, at least three times, at least four times, or at least five times. A different IGF-1 variant or a combination thereof can be used in each cell treatment.

In some embodiments, the cardiac stem cells can be contacted with at least one additional cytokine as described above (other than IGF-1 or IGF-2) prior to administration, such as hepatocyte growth factor (HGF) or a variant thereof. In one embodiment, cardiac stem cells are contacted with at least one additional cytokine prior to contacting with IGF-1 or a variant thereof. In alternative embodiment, cardiac stem cells are contacted with at least one additional cytokine after treatment with IGF-2 or a variant thereof. In another embodiment, cardiac stem cells are contacted with at least one additional cytokine after treatment with IGF-1, but prior to treatment with IGF-2.

In any methods of the invention, the cardiac stem cells, after treatment with IGF-2 and/or IGF-1, and at least one optional cytokine described above (referred herein as treated cardiac stem cells), can be administered to a subject in need thereof. Modes of administration of cells to a heart tissue are well known to those of skill in the art. In methods of the invention, any suitable mode can be used, e.g., injection, implantation, catheterization and intracoronary administration. In one embodiment, the treated cardiac stem cells are administered to an area of a damaged heart tissue of the subject. As used herein "damaged heart tissue" refers to heart tissue cells which have been exposed to ischemic conditions, i.e. a condition characterized by a lack of oxygen supply to tissues of an organ due to inadequate perfusion. These ischemic conditions may be caused by a myocardial infarction, or other cardiovascular disease or related complaint. The lack of oxygen causes the death of the cells in the surrounding area, leaving an infarct, which will eventually scar. The terms "damaged heart tissue" and "damaged myocardium" have been used herein interchangeably.

The treated cardiac stem cells can be delivered to the heart by one or more administrations. In one embodiment, the treated cardiac stem cells are delivered by a single administration. In another embodiment, multiple administrations of the same or different populations of treated cardiac stem cells are delivered to the heart.

In some embodiments, administration of the treated cardiac stem cells to a subject in need thereof can be accompanied by the administration of one or more agent, e.g., IGF-2, IGF-1 or a cytokine, to the heart. Non-limiting examples of cytokines that can be administered include: stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor, hepatocyte growth factor (HGF), Interleukin-3, or any cytokine capable of the stimulating and/or mobilizing stem cells. In one embodiment, the cytokines are selected from HGF or a functional variant thereof.

In embodiments of the invention, IGF-2, IGF-1 or variants thereof, and/or at least one additional cytokine (e.g., HGF) can be delivered simultaneously with the treated cardiac stem cells. Alternatively, the administration of IGF-2, IGF-1 and/or additional cytokines can either precede or follow the administration of the treated cardiac stem cells by a specified time period. The time period can be at least about 1 minute, at least about 5 minutes, at least about 15 minutes, at least about 30 minutes, at least about 1 hour, at least about 3 hours, at least about 6 hours, at least about 12 hours, at least about 24 hours, at least about 36 hours, at least about 1 week, at least about 2 weeks, or at least about 1 month.

The treated cardiac stem cells and/or an agent such as IGF-2, IGF-1 and a cytokine can be administered to the heart of the subject in need thereof by injection. In one embodiment, the injection is intramyocardial. One of skill in the art would be well aware of advantages of delivering cardiac stem cells by intramyocardial injection as the heart is a functioning muscle. Intramyocardial injection minimizes the loss of the injected cardiac stem cells due to the contracting movements of the heart. Alternatively, the treated cardiac stem cells can be administered by injection transendocardially or trans-epicardially. This mode of injection allows the cytokines to penetrate the protective surrounding membrane. In one embodiment, a catheter-based approach is used to deliver the trans-endocardial injection. The use of a catheter precludes more invasive methods of delivery wherein the opening of the chest cavity would be necessitated. As one skilled in the art would appreciate, optimum time of recovery would be allowed by the more minimally invasive procedure. A catheter approach can involve the use of such techniques as the NOGA catheter or similar systems. The NOGA catheter system facilitates guided administration by providing electromechanic mapping of the area of interest, as well as a retractable needle that can be used to deliver targeted injections or to bathe a targeted area with a therapeutic. Any methods of the invention can be performed through the use of such a system to deliver injections. One of skill in the art will recognize alternate systems that also provide the ability to provide targeted treatment through the integration of imaging and a catheter delivery system that can be used with the methods of the invention. Information regarding the use of NOGA and similar systems can be found in, for example, Sherman (2003) Basic Appl. Myol. 13: 11-14; Patel et al (2005) The Journal of Thoracic and Cardiovascular Surgery 130:1631-38; and Perrin et al. (2003) Circulation 107: 2294-2302; the text of each of which are incorporated herein in their entirety. In another embodiment, the cardiac stem cells can be administered by an intracoronary route of administration. One of skill in the art will recognize other useful methods of delivery or implantation which can be utilized with the methods of the invention, including those described in Dawn et al. (2005) Proc. Natl. Acad. Sci. USA 102, 3766-3771, the contents of which are incorporated herein in their entirety.

In a further aspect of the invention, the cardiac stem cells after treatment with IGF-1 or a variant thereof are administered, e.g., by intramyocardial injection or a catheter, to a subject in need thereof; and then an effective amount of IGF-2 is administered, e.g., by intramyocardial injection or a catheter, to the subject thereafter. In one embodiment, IGF-2 or a variant thereof can be administered immediately after administration of IGF-1 treated cardiac stem cells to the subject. In some embodiments, IGF-2 administration can be performed any period of time, e.g., minutes, hours, days, weeks, or months, after administration of IGF-1-treated cells to the subject. The period of time can be about 1 minute to about 5 minutes, about 5 minutes to about 30 minutes, about 30 minutes to 1 hour, about 1 hour to 6 hours, about 6 hours to 12 hours, about 12 hours to about 1 day, about 1 day to about 1 week, about 1 week to about 1 month, or at least about 1 month, at least about 2 months, or at least about 3 months.

In embodiments of the invention, administration of treated cardiac stem cells can result in amelioration of at least one symptom associated with cardiovascular disease, e.g., heart failure, myocardial infarction, an age-related cardiomyopathy or a damaged myocardium. In one embodiment, at least one symptom of the cardiovascular disease is alleviated by at least about 10%, at least about 15%, at least about 20%, at least about 30%, at least about 40%, or at least about 50%. In one embodiment, at least one symptom is alleviated by more than 50%. In one embodiment, at least one symptom is alleviated by at least about 80%, at least about 90% or greater, as compared to the severity of symptoms in the absence of administration with treated hCSCs.

Cardiac Stem Cells

The term "cardiac stem cells" as used herein refer to cardiac cells that have the ability to renew themselves through mitosis as well as the ability to differentiate into more than one specialized cell type, such as cardiomyocytes, smooth muscle cells and endothelial cells, i.e. the cells are multipotent. In one embodiment, the cardiac stem cells express c-kit. In one embodiment, the cardiac stem cells express c-kit and are negative for hematopoietic markers including CD34, CD45, CD133, CD105, CD90 and multiple markers of bone marrow cell lineages. In one embodiment, cardiac stem cells are negative for cardiac transcription factors (e.g., Nkx2.5, MEF2C, GATA4, GATA6, Ets1) and cardiac cytoplasmic/membrane proteins (e.g. α-sarcomeric actin, α-smooth muscle actin, vWf, CD31). In some embodiments, cardiac stem cells are not precursors or progenitors although during differentiation they acquire markers of cardiovascular lineages.

In one embodiment, the cardiac stem cells are somatic stem cells. The term "somatic stem cells" as used herein generally refers to multipotent stem cells that are not derived from the germline (e.g., sperms or eggs) and that can differentiate into more than one cell type of an organ from which they originate, e.g., heart. In one embodiment, the somatic stem cells are stem cells derived from a heart tissue.

In some embodiments of the invention, a population of cardiac stem cells can be isolated from a myocardial tissue of the subject, e.g., as described in Bearzi C et al., 104 PNAS 14068 (2007). The term "population" as used herein refers to more than one cell with the same phenotypic characteristics. The phrase "a population of cardiac stem cells" as used herein refers to a collection of cells comprising more than one cardiac stem cell, e.g., at least about 10% cardiac stem cells, at least about 20% cardiac stem cells, at least about 30% cardiac stem cells, at least about 40% cardiac stem cells, at least about 50% cardiac stem cells, at least about 60% cardiac stem cells, at least about 70% cardiac stem cells, at least about 80% cardiac stem cells, at least about 90% cardiac stem cells, at least about 95%, about 98%, about 99% or 100% cardiac stem cells. Other cells that can be present in a population of cardiac stem cells can include, but are not limited to, cardiomyocytes, skeletal myoblasts, somatic stem cell, e.g., bone marrow stem cells, or any cells known in the art for supporting the survival and differentiation of cardiac stem cells to mature cardiomyocytes.

Methods for isolating cardiac stem cells are known in the art. Cardiac stem cells can be isolated from tissue specimens (e.g. myocardium or myocardial vessels) obtained from a subject or patient. By way of an example only, a myocardial tissue specimen can be minced and placed in appropriate culture medium. Cardiac stem cells growing out from the tissue specimens can be observed in approximately 1-2 weeks after initial culture. At approximately 4 weeks after the initial culture, the expanded stem cells can be collected by centrifugation. Other methods of isolating adult cardiac stem cells from a subject are known in the art and can be employed to obtain suitable stem cells for use in the methods of the invention. U.S. Patent Application Publication No. 2006/0239983, filed Feb. 16, 2006, which is incorporated herein by reference in its entirety, describes media appropriate for culturing and expanding adult stem cells, particularly human cardiac stem cells. However, one of ordinary skill in the art would be able to determine the necessary components and modify commonly used cell culture media to be employed in culturing the isolated cardiac stem cells that can be used in the methods, compositions and kits of the invention.

Cardiac stem cells (CSCs) can be obtained from a myocardial tissue of a subject. Methods for isolating and characterizing cardiac stem cells are described in U.S. Pat. App. Pub. No.: US 2009/0180998, US 2009/0148421, US 2009/0162329 and U.S. Pat. No. 7,547,674, the contents of which are incorporated herein by reference in their entirety. In the case of an autologous CSC donation, CSCs can be obtained from a fresh surgical sample, such as a cardiac biopsy performed for a clinical indication. The term "autologous" as used herein refers to an object that is derived or transferred from the same individual's body, e.g., autologous blood donation, autologous bone marrow transplant. In the case of an allogenic CSC donation, CSCs can be obtained from a surgical sample, such as a cardiac biopsy from a patient undergoing therapeutic transplantation or a donor heart not utilized for transplantation. As used herein, the term "allogeneic" refers to an object that is genetically different although belonging to or obtained from the same species, e.g., a human. The surgical sample or biopsy may be obtained from the right ventricle (RV), interventricular septum, left ventricle (LV), or any other region of the cardiac tissue that comprises cardiac stem cells. In one embodiment, the surgical sample is about 1 to about 5 grams in size. In another embodiment, the surgical sample is less than 1 gram in size. In some embodiments, CSCs can be found in regions of the atrium of a subject that are normally discarded during routine cardiac surgery. The cardiac stem cells described herein can be obtained by mechanically and enzymatically dissociating cells from human myocardial tissue present in the sample. Mechanical dissociation can be brought about using methods that include, without limitation, chopping and/or mincing the tissue, and/or centrifugation and the like. Enzymatic dissociation of connective tissue and from cell-to-cell associations can be brought about by enzymes including, but not limited to, Blendzyme, DNAse I, collegenase and trypsin, or a cocktail of enzymes found to be effective in liberating cardiac stem cells from the cardiac sample. The procedure for mechanically and enzymatically isolating a cardiac stem cell should not be construed to be limited to the materials and techniques presented herein, but rather it will be recognized that these techniques are well-established and fall well within the scope of experimental optimization performed routinely in the art.

In one embodiment, the cardiac stem cells described herein is lineage negative. The term "lineage negative" is known to one skilled in the art as a cell that does not express antigens characteristic of specific cell lineages. Lineage negative stem cells can be isolated by various means, including but not limited to, removing lineage positive cells by contacting a cell population with antibodies against lineage markers and subsequently isolating the antibody-bound cells by using an anti-immunoglobulin antibody conjugated to magnetic beads and a biomagnet. Alternatively, the antibody-bound lineage positive cells may be retained on a column containing beads conjugated to anti-immunoglobulin antibodies. The cells not bound to the immunomagnetic beads represent the lineage negative stem cell fraction and can be isolated. For instance, cells expressing markers of the cardiac lineage (e.g. markers of vascular cell or cardiomyocyte commitment) can be removed from the cell populations in order to isolate lineage negative cardiac stem cells. Markers of the vascular lineage include, but are not limited to, GATA6 (SMC transcription factor), Ets1 (EC transcription factor), Tie-2 (angiopoietin receptors), VE-cadherin (cell adhesion molecule), CD62E/E-selectin (cell adhesion molecule), alpha-SM-actin (α-SMA, contractile protein), CD31 (PECAM-1), vWF (carrier of factor VIII), *Bandeiraera simplicifolia* and *Ulex europaeus* lectins (EC surface glycoprotein-binding molecules). Markers of the myocyte lineage include, but are not limited to, GATA4 (cardiac transcription factor), Nkx2.5 and MEF2C (myocyte transcription factors), and alpha-sarcomeric actin (α-SA, contractile protein).

In certain embodiments, the lineage negative cardiac stem cells express the stem cell surface marker, c-kit, which is the receptor for stem cell factor. Positive selection methods for isolating a population of lineage negative stem cells expressing c-kit are well known to the skilled artisan. Examples of possible methods include, but are not limited to, various types of cell sorting, such as fluorescence activated cell sorting (FACS) and magnetic cell sorting as well as modified forms of affinity chromatography. In one embodiment, the lineage negative stem cells are c-kit positive.

In some embodiments of the invention, cardiac stem cells express IGF-1 receptor (IGF-1R). In some embodiments, cardiac stem cells express IGF-2 receptor (IGF-2R). In some embodiments, cardiac stem cells express angiotensin type 1 receptor (AT1R). The inventors have discovered that the percentage of human cardiac stem cells positive for IGF-1R decreased with aging, while fraction of cells expressing IGF-2R and AT1R increased (Example 4). Since IGF-1R-positive hCSCs show higher growth reserve, as compared to hCSCs expressing IGF-2R-positive or AT1R-positive cells, IGF-1R expression can be assessed in the cardiac stem cells. The IGF-1 receptor is a surface protein and can be detected by routine methods known to the skilled artisan to measure expression of surface markers. Such methods include, but are not limited to FACS, magnetic cell sorting, and modified forms of affinity chromatography. Alternatively, IGF-1 receptor expression can be measured by immunocytochemistry or Western blotting techniques. In one embodiment, cardiac stem cell clones positive for IGF-1 receptor expression are selected for use in methods of the invention. In such embodiments, the cardiac stem cells can be negative for IGF-2R and/or AT1R. In some embodiments, the cardiac stem cells express ligands for those receptors, e.g., IGF-1, IGF-2, angiotensin II (Ang II), or a combination thereof.

In some embodiments, the population of cardiac stem cells can further comprise vascular progenitors cells (VPCs) and myocyte progenitor cells (MPCs). Vascular progenitor cells can be isolated from a c-kit positive stem cell population, as described above, by selecting cells expressing the VEGFR2 receptor, flk1. Vascular progenitor cells are lineage negative, c-kit positive, and flk1 positive. Similarly, myocyte progenitor cells can be isolated from the c-kit positive stem cell population by selecting cells that do no express flk1. Myocyte progenitor cells are lineage negative, c-kit positive, and flk1 negative. Similar methods for isolating c-kit positive stem cells can be employed to select cells that express or do not express the flk1 receptor (e.g. immunobeads, cell sorting, affinity chromatography, etc.).

Isolated lineage negative, c-kit positive stem cells can be plated individually, for instance, in single wells of a cell culture plate, and further expanded to obtain clones from individual stem cells.

In one embodiment, telomere length is measured in the clones derived from single stem cells. Methods of determining telomere length are well known in the art. Telomere length may be assessed by using methods such as quantitative fluorescence in situ hybridization (Q-FISH), Southern Blot, or quantitative PCR. Cardiac stem cells with telomeres that are at least 5 kbp, at least 8 kbp, at least 10 kbp, at least 12 kbp, at least 13 kbp, at least 14 kbp, at least 15 kbp, at least 16 kbp, at least 17 kbp, or at least 18 kbp in length can be selected for use or further expansion in cell culture. In one embodiment, human cardiac stem cells with telomeres that are at least 5 kbp in length are selected for further use.

In another embodiment, telomerase activity is measured in the expanded cardiac stem cell clones. Methods of measuring telomerase activity can include electrophoretic and ELISA-based telomere repeat amplification protocol (TRAP) assays as well as real time PCR methods. Telomerase activity in the isolated cardiac stem cells can be compared to that in control cells. The control cells can be freshly isolated c-kit positive cardiac cells from young animals. In the case of human cardiac stem cells, the control cells can be freshly isolated c-kit positive cardiac cells from a young (20-40 years) individual. Cardiac stem cells expressing at least 60%, at least 70%, at least 80%, preferably 90%, or 95% of the telomerase activity as compared to control cells can be selected for use and further expansion.

In some embodiments, the expanded cardiac stem cells can further differentiate into more than one specific cell type, e.g., cardiomyocytes, endothelial cells or smooth muscle cell in vitro, by contacting them with at least one cardiac cytokine essential for cell differentiation, e.g., IGF-2, using the methods of the invention. In some embodiments, at least about 20%, at least about 30%, at least about 40%, at least about 50%, at least about 60%, at least about 70%, at least about 80%, at least about 90%, at least about 95%, about 98%, about 99%, or 100% of the cardiac stem cells differentiate into cardiomyocytes, smooth muscle cells and/or endothelial cells in vitro.

In some embodiments, the cardiac stem cells can be derived from bone marrow stem cells or induced pluripotent stem cells of a subject, e.g., induced to have the characteristics of cardiac stem cells described herein. The bone marrow stem cells or induced pluripotent stem cells can be autologous or allogeneic.

IGF-1, IGF-2 and Variants Thereof

In accordance with aspects of the invention, cardiac stem cells can be contacted with IGF-1 or a variant thereof prior to IGF-2 or a variant thereof. In one embodiment, IGF-1 or a variant thereof is employed to expand the pool of functionally-competent stem cells. As used herein, the term "functionally-competent stem cells" refer to stem cells that retain the ability to divide many times over without showing replicative senescence, which can be determined by their telomere length and telomere activity as described above.

Insulin-like growth factor-1 (IGF-1) is known in the art by other aliases as insulin-like growth factor 1, MGF, IGF-IA, IGF-IB, somatomedin-C, OTTHUMP00000195082, OTTHUMP00000195084, mechano growth factor, insulin-like growth factor I, insulin-like growth factor IA, and insulin-like growth factor IB. The amino acid sequence of IGF-1 has been assigned a NCBI accession number for different species such as human, mouse and rat. In particular, the NCBI accession numbers for the amino acid sequences of human IGF-1 are NP_001104753 (SEQ ID NO: 1) or NP_001104754 (SEQ ID NO: 2), NP_001104755 (SEQ ID NO: 3) or NP_000609 (SEQ ID NO: 4), each of which represents a different preprotein isoform due to alternative splicing at the 5' and 3' ends of the IGF-1 gene. However, all isoforms produce an identical mature form of IGF-1. The conserved domain of IGF-1 is known to be located at aa49-116 of SEQ ID NO: 1, aa33-100 of SEQ ID NO: 2, aa49-116 of SEQ ID NO: 3, or aa49-116 of SEQ ID NO: 4. Thus, one of skill in the art can design a variant of IGF-1, which can bind to and activate IGF-1 receptor. In certain embodiments, an IGF-1 variant has an amino acid sequence that is at least 70% identical to an amino acid sequence of the conserved domain as set forth in SEQ ID NO: 1, 2, 3 or 4. In some embodiments, an IGF-1 variant has an amino acid sequence at least 85%, 90%, 95%, 97%, 98%, 99% or 100% identical to an amino acid sequence of the conserved domain as set forth in SEQ ID NO: 1, 2, 3 or 4.

In methods of the invention, cardiac stem cells are contacted with an effective amount of IGF-1 or a variant thereof. Various established in vitro assays can be used to determine an effective amount of IGF-1 or a variant thereof for treating cardiac stem cells. For example, after contacting the population of cardiac stem cells with an amount of IGF-1, or a variant thereof, for a specific amount of time, a subset of the treated cells can be used for in vitro characterization, e.g., proliferation assay, while the rest of the treated cardiac stem cells can be used for further treatment. The phrase "effective amount" as used herein refers to an amount of a compound, material, or composition which is effective for producing some desired effect in at least a sub-population of cells. For example, a population of cardiac stem cells is contacted with an amount of IGF-1, or a variant thereof, sufficient to produce a statistically significant, measurable response as described in Examples 2 and 5, when compared to cardiac stem cells in the absence of IGF-1 or a variant thereof. An exemplary measurable response is enhanced proliferation of cardiac stem cells in response to IGF-1, which can be determined by well-known BrdU labeling, e.g., described in Pang L et al., 197 Journal of Cellular Physiology. 251 (2003), and the BrdU labeling and immunocytochemisty protocol available at Millipore website: http://www.millipore.com/cellbiology/cb3/brdulabeling.

Accordingly, in one embodiment, the effective amount of IGF-1 or a variant thereof is sufficient to increase proliferation of the cardiac stem cells, e.g., detected by BrdU labeling of CSCs for a specific amount of time such as about 12 hours, by at least about 10%, at least about 20%, at least about 30%, at least about 40%, at least about 50%, at least about 60%, at least about 70%, at least about 80%, at least about 90%, about 95%, about 98%, about 99% or 100%, as compared to cardiac stem cells in the absence of IGF-1 or a variant thereof.

Other methods that can be used to indicate proliferation of cardiac stem cells in response to IGF-1 is measurement of population doubling time. Accordingly, in one embodiment, the effective amount of IGF-1 or a variant thereof is sufficient to shorten the population doubling time of CSC by at least about 10%, at least about 20%, at least about 30%, at least about 40%, at least about 50%, at least about 60%, at least about 70%, at least about 80%, at least about 90%, about 95%, about 98%, about 99% or 100%, as compared to cardiac stem cells in the absence of IGF-1 or a variant thereof.

In another embodiment, the effective amount of IGF-1 is sufficient to increase an amount of mTOR-Rictor complex (TORC1) by at least about 10%, at least about 20%, at least about 30%, at least about 40%, at least about 50%, at least about 60%, at least about 70%, at least about 80%, at least about 90%, about 95%, about 98%, about 99% or 100%, as compared to cardiac stem cells in the absence of IGF-1 or a variant thereof. Commercial antibodies for TORC1 are available through Cell Signaling, Novus Biologicals, etc., for western blotting and immunostaining. A skilled artisan can readily measure the level of TORC1 using the established protocols in the art.

In one embodiment, the effective amount of IGF-1 or a variant thereof is about 0.1 ng/ml to about 400 ng/ml. In some embodiments, the effective amount of IGF-1 or a variant thereof can be present in an amount of about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml or about 400 ng/ml. In one embodiment, the effective amount of IGF-1 or a variant thereof is about 100 ng/ml. In one embodiment, the effective amount of IGF-1 or a variant thereof is at least about 50 ng/ml, at least about 100 ng/ml, or at least about 150 ng/ml.

IGF-1 promotes CSC proliferation while IGF-2 favors CSC differentiation to mature cardiomyocytes. In embodiments of the invention, cardiac stem cells are contacted with IGF-2. In one embodiment, the cardiac stem cells are contacted with an effective amount of IGF-2 after treatment with IGF-1. In accordance with the invention, IGF-2 is employed to enhance myocyte formation and hCSC differentiation to mature cardiomyoctyes. IGF-2 is known in the art by aliases as PP1446, C11orf43, FLJ22066, FLJ44734, IGF-II, PP9974, OTTHUMP00000220677, insulin-like growth factor II, insulin-like growth factor type 2, somatomedin-A. The amino acid sequence of IGF-2 has been assigned a NCBI accession number for different species such as human, mouse and rat. In particular, the NCBI accession numbers for the amino acid sequences of human IGF-2 are NP_000603 (SEQ ID NO: 5), NP_001007140 (SEQ ID NO: 6) or NP_001121070 (SEQ ID NO: 7). SEQ ID NO: 5 and SEQ ID NO: 6 encode the same isoform I, but SEQ ID NO: 6 has a different 5'UTR from the SEQ ID NO: 5, while SEQ ID NO: 7 encodes isoform II. The conserved domain of IGF-2 is known in the art to be located at aa28-91 of SEQ ID NO: 5, aa28-91 of SEQ ID NO: 6, or aa84-147 of SEQ ID NO: 7. Thus, one of skill in the art can design a variant of IGF-2, which can bind to and activate IGF-1 receptor. In certain embodiments, an IGF-2 variant has an amino acid sequence that is at least 70% identical to an amino acid sequence of the conserved domain as set forth in SEQ ID NO: 5, 6, or 7. In some embodiments, an IGF-2 variant has an amino acid sequence at least 85%, 90%, 95%, 97%, 98%, 99% or 100% identical to an amino acid sequence of the conserved domain as set forth in SEQ ID NO: 5, 6, or 7.

An effective amount of IGF-2 for treatment of CSCs prior to administration to a subject in need thereof, can be determined by in vitro assays. In one embodiment, an effective amount of IGF-2 is sufficient to increase expression of at least one marker for myocyte differentiation by at least about 10%, at least about 20%, at least about 30%, at least about 40%, at least about 50%, at least about 60%, at least about 70%, at least about 80%, at least about 90%, about 95%, about 98%, about 99% or 100%, as compared to cardiac stem cells in the absence of IGF-2 or a variant thereof. Non-limiting examples of markers for myocyte differentiation include α-sarcomeric actin, connexin-43, Nkx2.5, GATA-4 and MEF2C. A skilled artisan will be able to measure expression of these makers for myocyte differentiation by quantitative real-time polymerase chain reaction (qRT-PCR), immunolabeling and confocal microscopy as discussed in Example 6.

In another embodiment, an effective amount of IGF-2 is sufficient to increase an amount of mTOR-Raptor (TORC2) by at least about 10%, at least about 20%, at least about 30%, at least about 40%, at least about 50%, at least about 60%, at least about 70%, at least about 80%, at least about 90%, about 95%, about 98%, about 99% or 100%, as compared to cardiac stem cells in the absence of IGF-2 or a variant thereof. Commercial antibodies for TORC2 are available through Cell Signaling, Novus Biologicals, etc., for western blotting and immunostaining. A skilled artisan can readily measure the level of TORC2 using the established protocols in the art.

In one embodiment, the effective amount of IGF-2 or a variant thereof is about 0.1 ng/ml to about 400 ng/ml. In some embodiments, the effective amount of IGF-2 or a variant thereof can be present in an amount of about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml or about 400 ng/ml. In one embodiment, the effective amount of IGF-2 or a variant thereof is about 100 ng/ml. In one embodiment, the effective amount of IGf-2 or a variant thereof is at least about 50 ng/ml, at least about 100 ng/ml or at least about 150 ng/ml.

IGF-1 and IGF-2 are ligands for IGF-1 receptor (IGF-1R). They activate the IGF-1 receptor by binding to the protein tyrosine kinase of IGF-1R. Accordingly, IGF-1R agonists can also be used in the methods of the invention. The term "agonist" refers to a ligand to IGF-1 receptor that, when it binds to the receptor, activates the normal biochemical and physiological events triggered by binding of the natural ligand for the receptor (i.e, IGF-1 or IGF-2 for the IGF-1 receptor). In particular embodiments, an agonist has at least 20%, at least 30%, or at least 50% of the biological activity of the natural ligand. The activity of an IGF-1 receptor ligand can be measured in vitro by the measuring the extent of autophosphorylation of the receptor in response to ligand binding as described in Satyamarthy, K., et al., 2001, Cancer Res. 61:7318. MAP kinase phosphorylation can also be measured for the IGF-1 receptor (Satyamarthy, K., et al., 2001, Cancer Res. 61:7318).

Non-limiting examples of IGF-1 receptor agonists include variants of IGF-1 that activate the receptor but have reduced affinity for the soluble IGF-1 binding proteins, such as those disclosed in U.S. Pat. No. 4,876,242. IGF binding proteins are natural serum proteins that bind to IGF-1, holding it in circulation and extending its biological half-life. Thus, in some embodiments, the IGF-1 receptor ligand or agonist has reduced affinity for soluble IGF-1 binding proteins, as compared to native IGF-1. Binding affinity for the soluble IGF-1 binding proteins can be measured by a competition binding assay against labeled IGF-1 (e.g., I-125-IGF-1), using a mixture of purified IGF-1 binding proteins or rat L6 myoblast-conditioned medium (a naturally produced mixture of IGF-1 binding proteins), as described in Francis, G. L., et al. (1992, J. Mol. Endocrinol. 8:213-223); Szabo, L. et al. (1988, Biochem. Biophys. Res. Commun. 151:207-214); and Martin, J. L. et al. (1986, J. Biol. Chem. 261:8754-8760). An exemplary variant IGF-1 with reduced affinity for soluble IGF-1 binding proteins is LONG-R3-IGF-1 (Francis, G. L., et al. 1992, J. Mol. Endocrinol. 8:213-223; Tomas, F. M. et al., 1993, J. Endocrinol. 137:413-421).

Generally, an IGF-1 receptor agonist includes any molecules that act as an agonist of IGF-1 receptor. Such IGF-1 receptor agonists include, but are not limited to, a protein, a peptide, a small organic molecule, a peptidomimetic, an agonistic antibody, and a nucleic acid.

In some embodiments, an IGF-1 receptor agonist can be a peptide, such as those which activate IGF-1 receptor tyrosine kinase function. These peptides are also referred to herein as IGF-1 receptor agonistic peptides. These agonistic peptides can specifically target the ligand-binding domain of IGF-1 receptor tyrosine kinase. IGF-1R is known by other aliases as CD221, IGFIR, IGFR, JTK13, MGC142170, MGC142172 and MGC18216, or other designations as IGF-I receptor, insulin-like growth factor I receptor, soluble IGF1R variant 1 and soluble IGF1R variant 2. The amino acid sequence of IGF-1R receptor has been assigned a NCBI accession number for different species such as human, mouse and rat. In particular, the NCBI accession number for the amino acid sequence of human IGF-1 receptor (IGF-1R) is NP_000866 (SEQ ID NO: 8). It is also known in the art that the binding domain of IGF-1R protein tyrosine kinase is located between aa992-1268 of SEQ ID NO:8. Further, the 3D crystal structure of IGF-1R ligand-binding domain (cd06062) has been publicly available at NCBI website. Thus, one of skill in the art can design agonistic peptides, proteins or variants thereof for activating IGF-1 receptor.

To determine whether an IGF-1R agonistic peptide behaves as an IGF-1 or IGF-2, biological responses (e.g., cell proliferation and differentiation) of CSCs to the IGF-1R agonistic peptide can be determined in vitro as described herein and compared to treatment of CSCs with IGF-1 or IGF-2. For example, if the IGF-1R agonistic peptide enhances CSC proliferation but fails to induce myocyte differentiation, the IGF-1R agonistic peptide generates biological responses as an IGF-1 ligand in CSCs, and thus it can be used as an IGF-1 variant.

In certain embodiments, the structure of an IGF-1R agonistic peptide can be modified for such purposes as enhancing therapeutic efficacy, or stability (e.g., ex vivo shelf life or resistance to proteolytic degradation in vivo). Modified IGF-1R agonistic peptides can be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an IGF-1R agonistic peptide results in a functional homolog can be readily determined by assessing the ability of the variant IGF-1R agonistic peptide to produce a response (e.g., cell proliferation detected by well-established BrdU labeling) in cardiac stem cells in a fashion similar to the wild-type IGF-1R agonistic peptide.

In one embodiment, the effective amount of an IGF-1R agonist is about 0.1 ng/ml to about 400 ng/ml. In some embodiments, the effective amount of IGF-1R agonist can be present in an amount of about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml or about 400 ng/ml. In one embodiment, the effective amount of an IGF-1R agonist is at least about 50 ng/ml, at least about 100 ng/ml or at least about 150 ng/ml.

Compositions of the Invention

Another aspect of the invention encompasses compositions comprising at least one cardiac stem cell described herein and an effective amount of IGF-2 or a variant thereof. In some embodiments of the invention, the composition further comprises an effective amount of IGF-1 or a variant thereof. In additional embodiments, the composition can further comprise at least one additional cytokine as described herein (e.g., HGF).

In one embodiment, the composition further comprises a cell culture medium. As used herein, the term "cell culture medium" refers to any nutrient medium in which cardiac stem cells can be cultured in vitro. Examples of nutrients essential to cell metabolism and proliferation, e.g., amino acids, lipids, carbohydrates, vitamins and mineral salts can be included in the cell culture medium. In one embodiment, cell culture medium also comprises any substance essential to cell differentiation. One of skill in the art can determine an appropriate formulation of cell culture medium for culturing cardiac stem cells, based on the cell condition (e.g., morphology, viability, growth rate and cell density).

The composition of the invention can comprise a concentration of cardiac stem cells from about $2 \times 10^4$ cells to about $2 \times 10^7$ cells, about $1 \times 10^5$ cells to about $6 \times 10^6$ cells, or about $2 \times 10^6$ cells. In one embodiment, the composition can comprise a concentration of at least about $1 \times 10^4$ CSCs, at least about $5 \times 10^4$ CSCs, at least about $1 \times 10^5$ CSCs or at least about $1 \times 10^6$ CSCs. In one embodiment, the composition can comprise a concentration of cardiac stem cells from about $1 \times 10^4$ cells/ml to about $1 \times 10^8$ cells/ml, or $1 \times 10^5$ cells/ml to about $1 \times 10^7$ cells/ml. In one embodiment, the composition can comprise a concentration of at least about $0.5 \times 10^4$ CSCs per ml, at least about $5 \times 10^4$ CSCs per ml, at least about $1 \times 10^5$ CSCs per ml or at least about $1 \times 10^6$ CSCs per ml. Depending on the use of compositions of the invention, a skilled artisan can determine an appropriate concentration of the cardiac stem cells in a composition. For example, for cell culture compositions, e.g., comprising a cell culture medium, lower concentrations of cardiac stem cells, e.g., $2 \times 10^4$ cells-$2 \times 10^5$ cells can be selected for a culturing purpose. For therapeutic administration purpose, the composition of the invention can comprise higher concentrations of cardiac stem cells, e.g., about $1 \times 10^6$ cells to about $2 \times 10^6$ cells. The precise determination of an effective dose can be based on individual factors, including their size, age, size of the infarct, and amount of time since damage. Therefore, dosages can be readily adjusted for each individual patient by those skilled in the art.

For administration to a subject in need thereof, e.g., with a damaged myocardium, cardiac stem cells and IGF-2, or a variant thereof, can be provided in a pharmaceutically acceptable composition. In such embodiments, IGF-1 or a variant thereof can be optionally included. In embodiments of composition with IGF-1, IGF-2 is added after cardiac stem cells have been in contact with IGF-1. As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some embodiments, the pharmaceutical acceptable composition can include a population of cardiac stem cells that further comprises vascular progenitor cells (VPCs) and myocyte progenitor cells (MPCs) in a particular ratio. This ratio can be adjusted to generate more vascular tissue (i.e. a higher number of VPCs compared to MPCs) or more myocardium (i.e. a higher number of MPCs compared to VPCs). The ratio of VPCs to MPCs in the pharmaceutical composition may be 1:20; 1:10; 1:5, 1:2; 1:1:2:1, 5:1; 10:1, and 20:1. In a preferred embodiment, the ratio of VPCs to MPCs is 1:1.

The pharmaceutically acceptable composition can further comprise one or more pharmaceutical carriers (additives) and/or diluents. As used herein, the term "pharmaceutically-acceptable carrier" means a pharmaceutically-acceptable material, composition or vehicle, such as a liquid, diluent, excipient, manufacturing aid or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to, gelatin, buffering agents, pyrogen-free water, isotonic saline, Ringer's solution, pH buffered solutions, bulking agents such as polypeptides and amino acids, serum component such as serum albumin, HDL and LDL, and other non-toxic compatible substances employed in pharmaceutical formulations. Preservatives and antioxidants can also be present in the formulation. The terms such as "excipient", "carrier", "pharmaceutically acceptable carrier" or the like are used interchangeably herein.

Pharmaceutically acceptable carriers can vary in a composition of the invention, depending on the administration route and formulation. For example, the pharmaceutically acceptable composition of the invention can be delivered via injection. These routes for administration (delivery) include, but are not limited to, subcutaneous or parenteral including intravenous, intraarterial (e.g. intracoronary), intramuscular, intraperitoneal, intramyocardial, transendocardial, trans-epicardial, and infusion techniques. In one embodiment, the pharmaceutical acceptable composition is in a form that is suitable for myocardial injection. In another embodiment, the pharmaceutical composition is formulated for trans-epicardial or intracoronary injection.

When administering a pharmaceutical composition of the invention parenterally, it will be generally formulated in a unit dosage injectable form (solution, suspension, emulsion). The pharmaceutical formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS), with or without an agent, such as IGF-2, IGF-1 and/or any cytokine described herein.

In some embodiments, the pharmaceutical composition can be formulated in an emulsion or a gel. In such embodiments, at least one cardiac stem cell can be encapsulated within a biocompatible gel, e.g., hydrogel and a peptide gel, which is infused with IGF-2 or a variant thereof. In some embodiments, the CSC-containing biocompatible gel was infused with IGF-1 (or a variant thereof) for a sufficient amount of time to expand the CSC pool before perfusing the gel with IGF-2 (or a variant thereof). The gel pharmaceutical composition can be implanted to the border zone of the damaged myocardium of a subject.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it may be desirable to include isotonic agents, for example, sugars, sodium chloride, and the like.

The compositions can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions of the invention, however, any vehicle, diluent, or additive used should have to be biocompatible with cardiac stem cells.

The compositions can be isotonic, i.e., they can have the same osmotic pressure as blood and lacrimal fluid. The desired isotonicity of the compositions of the invention can be accomplished using sodium chloride, or other pharmaceutically acceptable agents such as dextrose, boric acid, sodium tartrate, propylene glycol or other inorganic or organic solutes. In one embodiment, sodium chloride is used in buffers containing sodium ions.

Viscosity of the compositions can be maintained at the selected level using a pharmaceutically acceptable thickening agent. In one embodiment, methylcellulose is used because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

In some embodiment, the compositions of the invention can be stored frozen. In such embodiments, an additive or preservative known for freezing cells can be included in the compositions. A suitable concentration of the preservative can vary from 0.02% to 2% based on the total weight although there may be appreciable variation depending upon the preservative or additive selected. One example of such additive or preservative can be dimethyl sulfoxide (DMSO) or any other cell-freezing agent known to a skilled artisan. In such embodiments, the composition will be thawed before use or administration to a subject.

Typically, any additives (in addition to the active cardiac stem cell(s), IGF-1, IGF-2 and/or cytokine(s)) can be present in an amount of 0.001 to 50 wt % solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, and about 0.05 to about 5 wt %. For any therapeutic composition to be administered to a subject in need thereof, and for any particular method of administration, it is preferred to determine toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan.

Those skilled in the art will recognize that the components of the compositions should be selected to be biocompatible with respect to cardiac stem cells and chemically and/or biologically inert to IGF-1, IGF-2 and/or optional cytokines. This will present no problem to those skilled in chemical and pharmaceutical principles, or problems can be readily avoided by reference to standard texts or by simple experiments (not involving undue experimentation).

The compositions of the invention can be prepared by mixing the ingredients following generally-accepted procedures. For example, isolated cardiac stem cells can be re-suspended in an appropriate pharmaceutically acceptable carrier and the mixture can be adjusted to the final concentration and viscosity by the addition of water or thickening agent and possibly a buffer to control pH or an additional solute to control tonicity. An effective amount of IGF-1 (or a variant thereof), IGF-2 (or a variant thereof), and/or any other additional cytokine can be mixed with the cell mixture. Generally the pH can vary from about 3 to about 7.5. In some embodiments, the pH of the composition can be about 6.5 to about 7.5. Compositions can be administered in dosages and by techniques well known to those skilled in the medical and veterinary arts taking into consideration such factors as the age, sex, weight, and condition of the particular patient, and the composition form used for administration (e.g., liquid). Dosages for humans or other mammals can be determined without undue experimentation by a skilled artisan.

Suitable regimes for initial administration and further doses or for sequential administrations can be varied. In one embodiment, a therapeutic regimen includes an initial administration followed by subsequent administrations, if necessary. In some embodiments, multiple administrations of cardiac stem cells can be injected to the subject's heart. For example, cardiac stem cells can be administered in two or more, three or more, four or more, five or more, or six or more injections. Injections can be made at the base of the heart, the apex, or the mid-region. In one embodiment, two injections of cardiac stem cells are administered at each of the apex, mid-region, and base. In one embodiment, more than one injection is administered to an area of a damaged heart tissue, e.g., the border of the area of the damaged heart tissue.

The subsequent injection can be administered immediately after the previous injection, or after at least about 1 minute, after at least about 2 minute, at least about 5 minutes, at least about 15 minutes, at least about 30 minutes, at least about 1 hour, at least about 2 hours, at least about 3 hours, at least about 6 hours, at least about 12 hours, at least about 24 hours, at least about 2 days, at least about 3 days, at least about 4 days, at least about 5 days, at least about 6 days or at least about 7 days. In some embodiments, the subsequent injection can be administered after at least about 1 week, at least about 2 weeks, at least about 1 month, at least about 2 years, at least about 3 years, at least about 6 years, or at least about 10 years.

After administration of the composition to a subject, at least one cardiac stem cell can become a myocardial cell and generated myocardium after at least about 30 minutes, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 1 day, at least about 2 days, at least about 3 days, at least about 1 week, at least about 2 weeks, or at least about 1 month. Methods for evaluating extent of myocardium regeneration, e.g., echocardiography, have been described in U.S. Pat. No. 7,547,674, the content of which is incorporated herein by reference in its entirety. Echocardiography, also known as cardiac ultrasound, allows 2D and 3D imaging of the heart, e.g., location and extent of damaged tissues, pumping capacity, motion of the heart wall and blood flow.

In further embodiments, at least one cardiac stem cell can differentiate into a cardiomyocyte forming functional myocardium, thereby increasing cardiac function. Increased cardiac function can be reflected as increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, and decreased wall tension. Assessment tests for cardiac functions are well known to a skilled practitioner. Exemplary tests for cardiac function include, but not limited to, echocardiography, electrocardiogram, X-ray, magnetic resonance imaging, coronary catheterization, and heart CT scan. A skilled practitioner, e.g., cardiologist, can adjust the therapeutic number of cardiac stem cells and effective amount of IGF-2 and/or IGF-1 in each pharmaceutical composition and/or determine the need for subsequent administrations by performing various cardiac function tests known in the art on the subject who has received the composition of the invention, and comparing the test results to those measured in the same subject prior to administration. In some embodiments, a dosage comprising a composition of the invention is considered to be pharmaceutically effective if the dosage improves cardiac function, e.g., increased exercise capacity, by at least about 10%, at least about 15%, at least about 20%, at least about 30%, at least about 40%, or at least about 50%. In one embodiment, the cardiac function is improved by more than 50%, e.g., at least about 60%, or at least about 70%. In another embodiment, the cardiac function is improved by at least about 80%, at least about 90% or greater, as compared to a control (e.g. in the absence of the composition described herein).

In some circumstances, one or more symptoms associated with cardiovascular diseases, e.g., heart failure, myocardial infarction, an age-related cardiomyopathy or a damaged myocardium, can be reduced or alleviated following administration of compositions of the invention. Symptoms of heart failure include, but are not limited to, fatigue, weakness, rapid or irregular heartbeat, dyspnea, persistent cough or wheezing, edema in the legs and feet, and swelling of the abdomen. Symptoms for myocardial infarction include, but are not limited to, prolonged chest pain, heart palpitations (i.e. abnormality of heartbeat), shortness of breath, and extreme sweating. Non-limiting symptoms of an age-related cardiomyopathy, e.g., restrictive cardiomyopathy, include coughing, difficulty breathing during normal activities or exercise, extreme fatigue, and swelling in the abdomen as well as the feet and ankles. In some embodiments, a dosage comprising a composition of the invention is considered to be pharmaceutically effective if the dosage alleviates at least one symptom of cardiovascular disease described above by at least about 10%, at least about 15%, at least about 20%, at least about 30%, at least about 40%, or at least about 50%. In one embodiment, at least one symptom is alleviated by more than 50%, e.g., at least about 60%, or at least about 70%. In another embodiment, at least one symptom is alleviated by at least about 80%, at least about 90% or greater, as compared to a control (e.g. in the absence of the composition described herein).

A further aspect of the invention relates to kits for treating at least one cardiac stem cell to be administered to as a subject in need thereof. In one embodiment, the kit comprises a composition of the invention, instruction for culturing the composition, and optionally cell culture supply, e.g., a cell culture flask, and/or cell culture medium, and/or at least one additional cytokine described herein. In another embodiment, the kit comprises a pharmaceutical composition, instructions for administering the pharmaceutical composition described herein, and optionally a delivery device and/or at least one additional agent, such as IGF-2, IGF-1 and/or a cytokine described herein. The additional agent can be in the same pharmaceutical composition of the invention or they can be in separate pharmaceutical compositions packaged in different containers within the kit. The delivery devices that can be optionally included in the kit include a catheter, syringe, or any other appropriate delivery device.

Selection of Subjects in Need Thereof

Yet another aspect of the invention relates to the use of methods, compositions and kits described herein to increase proliferation and differentiation of cardiac stem cells to be administered to a subject in need thereof. The inventors have demonstrated that activation of CSCs with IGF-2 can promote their differentiation to mature cardiomyocytes and in turn enhances myocardium regeneration in an in vivo mouse model, as compared to in the absence of IGF-2 (Example 10).

Accordingly, methods, compositions and kits of the invention can be used for treatment of cardiovascular disease, including, but not limited to, atherosclerosis, ischemia, hypertension, restenosis, angina pectoris, rheumatic heart disease, congenital cardiovascular defects, age-related cardiomyopathy, and arterial inflammation and other disease of the arteries, arterioles and capillaries. In one embodiment, the methods, compositions and kits of the invention provide for the repair and/or regeneration of a damaged myocardium resulting from one of the diseases listed above or from the general decline of myocardial cells with age.

The terms "treatment" and "treating" as used herein, with respect to treatment of a disease, means preventing the progression of the disease, or altering the course of the disorder (for example, but are not limited to, slowing the progression of the disorder), or reversing a symptom of the disorder or reducing one or more symptoms and/or one or more biochemical markers in a subject, preventing one or more symptoms from worsening or progressing, promoting recovery or improving prognosis. For example, in the case of treating cardiovascular disease, e.g., myocardial infarction, therapeutic treatment refers to improved cardiac function described herein after administration of the composition of the invention. In another embodiment, the therapeutic treatment refers to alleviation of at least one symptom associated with cardiovascular disease, e.g., myocardial infarction. Measurable lessening includes any statistically significant decline in a measurable marker or symptom, such as measuring cardiac biomarkers, such as cardiac troponin I in the blood, assessing the swelling in the arm or leg, or assessing the cardiac function with electrophysiological tests such as echocardiography (as described in detail below) after treatment. In one embodiment, at least one symptom of cardiovascular disease, e.g., myocardial infarction, is alleviated by at least about 10%, at least about 15%, at least about 20%, at least about 30%, at least about 40%, or at least about 50%. In another embodiment, at least one symptom is alleviated by more than 50%, e.g., at least about 60%, or at least about 70%. In one embodiment, at least one symptom is alleviated by at least about 80%, at least about 90% or greater, as compared to a control (e.g. in the absence of the composition described herein).

In one embodiment, subjects in need thereof are selected prior to administering the compositions or kits of the invention or employing the methods described herein. In some embodiments, the subject in need thereof can be diagnosed with or suffering from a damaged myocardium. In another embodiment, the subject in need thereof can be diagnosed with or suffering from a myocardial infarction. In certain embodiment, the subject in need thereof can be diagnosed with or suffering a heart failure. In some embodiments, the subject in need thereof can be diagnosed with or suffering from an age-related cardiomyopathy. As used herein, the term "age-related cardiomyopathy" refers to the deterioration of the myocardium (heart muscle tissue) as a result of intrinsic mechanisms occurring as a subject ages. An example of age-related cardiomyopathy is restrictive cardiomyopathy.

A set of guidelines for diagnosis of heart diseases, e.g., myocardial infarction, has been proposed jointly by the American college of Cardiologists and the Europe School of Cardiology (ACC/ESC; Alpert et al. 2000). These guidelines emphasize the importance of changes in the levels of the biochemical markers cardiac troponin I (cTnI) and creatine kinase MB form (CK-MB), in combination with other diagnostic factors such as electrocardiogram (ECG) results, especially ST segment elevation, but also ST segment depression or T-wave inversion, and typical symptoms of severe chest pain and dyspnoea.

To diagnose for ischemic heart disease in a subject, an electrocardiogram can be performed. An electrocardiogram (ECG) is a recording of the electrical activity of the heart. Abnormalities in the electrical activity usually occur with heart attacks and can identify the areas of heart muscle that are deprived of oxygen and/or areas of muscle that have died. In some patients, the diagnosis can be made through detection of elevated cardiac enzymes in the blood. Cardiac enzymes are proteins that are released into the blood by dying heart muscles. These cardiac enzymes are creatine phosphokinase (CPK), special sub-fractions of CPK (specifically, the MB fraction of CPK), and troponin, and their levels can be measured in blood. These cardiac enzymes typically are elevated in the blood several hours after the onset of a heart attack. A series of blood tests for the enzymes performed over a 24-hour period are useful not only in confirming the diagnosis of heart attack, but the changes in their levels over time also correlates with the amount of heart muscle that has died. The B-type of natriuretic peptide (BNP) together with pro-BNP, NT-proBP (EP1363128, EP1666881) has also proven to be a further effective biochemical marker in myocardial diagnostics. Other biomarkers that can be used for diagnosis of heart diseases, e.g., myocardial infarction, include, but are not limited to, the ones disclosed in US Pat. App. Pub. Nos: US 2009/0208986, US 2010/0151504 and PCT App. No.: WO 2006/120391, the contents of which are incorporated herein by their entirety.

Heart diseases can be diagnosed with any methods known to a skilled practitioner, e.g., chest X-ray, or monitoring heart rate, blood pressure and electrocardiogram during exercise stress test. Other tests for diagnosis of heart disease include, but are not limited to, an echocardiogram that uses ultrasound to evaluate one's heart muscle, heart valves, and risk for heart disease; cardiac catheterization (also called cardiac cath or coronary angiogram) that allows a physician to "see" how well one's heart is functioning; an electrophysiology (EP) study that records the electrical activity and the electrical pathways of one's heart; cardiac computed tomography (CT) that uses CT technology with or without intravenous (IV) contrast (dye) to visualize the heart anatomy, coronary circulation, and great vessels (which includes the aorta, pulmonary veins, and arteries); a heart biopsy (also called myocardial biopsy or cardiac biopsy) that involves using a bioptome (a small catheter with a grasping device on the end) to obtain a small piece of heart muscle tissue that is sent to a laboratory for analysis; and MRI (magnetic resonance imaging) that obtains information about the heart as it is beating, creating images of the heart throughout its pumping cycle. Other imaging methods, e.g., magnetic resonance imaging, for diagnosis of heart diseases disclosed in U.S. Pat. Nos.: U.S. Pat. No. 3,951,140, 6,205, 349 and U.S. Pat. No. 4,867,963 (the contents of which are incorporated herein by their entirety), are also included within the scope of the invention.

In some embodiments, the subject selected for the methods described herein can be previously diagnosed with a damaged myocardium and is now recovered. In other embodiments, the subject selected for the methods described herein can have undergone other cardiac interventions.

As used herein, a "subject" can mean a human or an animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. A patient or a subject includes any subset of the foregoing, e.g., all of the above, or includes one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

In one embodiment, the subject is a mammal. The mammal can be a human, non-human primate, mouse, rat, dog, cat, horse, or cow, but are not limited to these examples. Mammals other than humans can be advantageously used as subjects that represent animal models of stem cell therapy for repair for damaged myocardium. In addition, the methods and compositions described herein can be employed in domesticated animals and/or pets.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the paragraphed invention, because the scope of the invention is limited only by the paragraphs. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "administer" or "administration" refers to the placement of a composition into a subject by a method or route which results in at least partial localization of the composition at a desired site such that desired effect is produced. Routes of administration suitable for the methods of the invention include, but are not limited to, injection and delivery by a catheter. Generally, local administration results in more of the composition being delivered to a specific location as compared to the entire body of the subject.

The term "hydrogel" as used herein refers to natural or synthetic polymers that show superabsorbent properties (having even over 99% water) and possess a degree of flexibility similar to natural tissue, due to their significant water content. Examples of hydrogels used as scaffolds in tissue engineering or reservoirs in local drug delivery include, but are not limited to, methylcellulose, hylaronan, and other naturally derived polymers. In one embodiment, the hydrogel is biodegradable.

The term "increase" or "enhance" as used herein generally means an increase by a statistically significant amount. In one embodiment, "increase" or "enhance" refers to an increase by at least 10% as compared to a reference level, for example an increase by at least about 20%, or at least about 30%, or at least about 40%, or at least about 50%, or at least about 60%, or at least about 70%, or at least about 80%, or at least about 90% or up to and including a 100% increase, or any increase between 10-100% as compared to a reference level. The reference level as used herein refers to a control in the absence of, e.g., IGF-2. In one embodiment, the reference level is measured prior to administration of the composition described herein.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

The present invention may be defined in any of the following numbered paragraphs:

1. A method of treating cardiac stem cells to be administered to a subject in need thereof, comprising:
   a. contacting a population of cardiac stem cells with an effective amount of IGF-2 or a variant thereof;
   b. administering the population of cardiac stem cells from step (a) to the subject in need thereof;
2. The method of paragraph 1, wherein at least a subset of the population of cardiac stem cells express IGF-1 receptor.
3. The method of any of paragraphs 1-2, wherein the population of cardiac stem cells is administered to an area of a damaged heart tissue of the subject in need thereof
4. The method of any of paragraphs 1-3, wherein the population of cardiac stem cells is administered by injection.
5. The method of any of paragraphs 1-4, wherein the population of cardiac stem cells is administered by a catheter.
6. The method of any of paragraphs 1-5, wherein the population of cardiac stem cells is administered via an intracoronary route.
7. The method of any of paragraphs 1-6, wherein the effective amount is sufficient to increase expression of at least one marker for myocyte differentiation by at least about 10%, as compared to cardiac stem cells in the absence of IGF-2 or a variant thereof
8. The method of paragraph 7, wherein the marker for myocyte differentiation is selected from the group consisting of: α-sarcomeric actin, connexin-43, Nkx2.5, GATA-4 and MEF2C.
9. The method of any of paragraphs 1-8, wherein the effective amount of IGF-2 or a variant thereof is about 100 ng/mL.
10. The method of any of paragraphs 1-9, wherein the cardiac stem cells are contacted with IGF-2 or a variant thereof for an amount of time sufficient to increase myocyte formation, as compared to cardiac stem cells in the absence of IGF-2.
11. The method of any of paragraphs 1-10, wherein the cardiac stem cells are contacted with IGF-2 for an amount of time sufficient for the cardiac stem cells to confer acquisition of at least one adult cardiomyocyte phenotype, as compared to cardiac stem cells in the absence of IGF-2.
12. The method of paragraph 11, wherein the adult cardiomyocyte phenotype is selected from the group consisting of: a myocyte volume greater than 2000 $\mu m^3$, contractility in response to electric stimulation, an elongated morphology, calcium tolerance, expression of at least one contractile protein, and activation of ion current channels.

13. The method of paragraph 12, wherein the contractile protein is selected from the group consisting of: α-sarcomeric actin, myosin heavy chains, myosin light chains and tropomyosin.

14. The method of any of paragraphs 1-13, wherein the cardiac stem cells are contacted with IGF-2 or a variant thereof for about 2 hours.

15. The method of any of paragraphs 1-14, wherein the subject in need thereof has a damaged myocardium.

16. The method of any of paragraphs 1-15, wherein the subject in need thereof is diagnosed with or suffering from a myocardial infarction.

17. The method of any of paragraphs 1-16, wherein the subject in need thereof is diagnosed with or suffering from a heart failure.

18. The method of any of paragraphs 1-17, wherein the subject in need thereof is diagnosed with or suffering from an age-related cardiomyopathy.

19. The method of any of paragraphs 1-18, wherein the subject is a mammal.

20. The method of paragraph 19, wherein the mammal is a human.

21. The method of any of paragraphs 1-20, wherein the cardiac stem cells are isolated from a myocardial tissue of the subject.

22. A method of treating cardiac stem cells to be administered to a subject in need thereof, comprising:
    a. contacting a population of cardiac stem cells with an effective amount of IGF-1 or a variant thereof;
    b. contacting the population of cardiac stem cells from step (a) with an effective amount of IGF-2 or a variant thereof;
    c. administering the population of cardiac stem cells from step (b) to the subject in need thereof.

23. The method of paragraph 22, wherein at least a subset of the population of cardiac stem cells express IGF-1 receptor.

24. The method of any of paragraphs 22-23, wherein the effective amount of IGF-1 or a variant thereof is sufficient to increase proliferation of the cardiac stem cells by at least about 10%, as compared to cardiac stem cells in the absence of IGF-1.

25. The method of any of paragraphs 22-24, wherein the effective amount of IGF-1 or a variant thereof is about 100 ng/mL.

26. The method of any of paragraphs 22-25, wherein the cardiac stem cells are contacted with IGF-1 for at least about 12 hours.

27. The method of any of paragraphs 22-26, wherein the effective amount of IGF-2 is sufficient to increase expression of at least one marker for myocyte differentiation by at least about 10%, as compared to cardiac stem cells in the absence of IGF-2.

28. The method of paragraph 27, wherein the marker for myocyte differentiation is selected from the group consisting of: α-sarcomeric actin, connexin-43, Nkx2.5, GATA-4 and MEF2C.

29. The method of any of paragraphs 22-28, wherein the effective amount of IGF-2 or a variant thereof is about 100 ng/mL.

30. The method of any of paragraphs 22-29, wherein the cardiac stem cells are contacted with IGF-2 for an amount of time sufficient to increase myocyte formation, as compared to cardiac stem cells in the absence of IGF-2.

31. The method of any of paragraphs 22-30, wherein the cardiac stem cells are contacted with IGF-2 for an amount of time sufficient for the cardiac stem cells to confer acquisition of at least one adult cardiomyocyte phenotype, as compared to cardiac stem cells in the absence of IGF-2.

32. The method of paragraph 31, wherein the adult cardiomyocyte phenotype is selected from the group consisting of: a myocyte volume greater than 2000 $\mu m^3$, contractility in response to electric stimulation, an elongated morphology, calcium tolerance, expression of at least one contractile protein, and activation of ion current channels.

33. The method of paragraph 32, wherein the contractile protein is selected from the group consisting of: α-sarcomeric actin, myosin heavy chains, myosin light chains and tropomyosin.

34. The method of any of paragraphs 22-33, wherein the population of cardiac stem cells is administered to an area of a damaged heart tissue of the subject in need thereof 35. The method of any of paragraphs 22-34, wherein the population of cardiac stem cells is administered by injection.

36. The method of any of paragraphs 22-35, wherein the population of cardiac stem cells is administered by a catheter.

37. The method of any of paragraphs 22-36, wherein the population of cardiac stem cells is administered via an intracoronary route.

38. The method of any of paragraphs 22-37, wherein the subject in need thereof has a damaged myocardium.

39. The method of any of paragraphs 22-38, wherein the subject in need thereof is diagnosed with or suffering from a myocardial infarction.

40. The method of any of paragraphs 22-39, wherein the subject in need thereof is diagnosed with or suffering from a heart failure.

41. The method of any of paragraphs 22-40, wherein the subject in need thereof is diagnosed with or suffering from an age-related cardiomyopathy.

42. The method of any of paragraphs 22-41, wherein the subject is a mammal.

43. The method of paragraph 42, wherein the mammal is a human.

44. The method of any of paragraphs 22-43, wherein the cardiac stem cells are isolated from a myocardial tissue of the subject.

45. A composition comprising at least one cardiac stem cell and an effective amount of IGF-2 or a variant thereof 46. The composition of paragraph 45, further comprising a pharmaceutically acceptable carrier.

47. The composition of paragraph 45, further comprising a cell culture medium.

48. The composition of any of paragraphs 45-47, wherein at least one cardiac stem cell expresses IGF-1 receptor.

49. The composition of any of paragraphs 45-48, wherein the effective amount of IGF-2 or a variant thereof is sufficient to increase expression of at least one marker for myocyte differentiation by at least about 10%, as compared to cardiac stem cells in the absence of IGF-2.

50. The composition of paragraph 49, wherein the marker for myocyte differentiation is selected from the group consisting of: α-sarcomeric actin, connexin-43, Nkx2.5, GATA-4 and MEF2C.

51. The composition of any of paragraphs 45-50, wherein the effective amount of IGF-2 or a variant thereof is about 100 ng/mL.

52. The composition of any of paragraphs 45-51, wherein the cardiac stem cell is isolated from a myocardial tissue of a subject.
53. A composition comprising at least one cardiac stem cell and an effective amount of IGF-1 and IGF-2, or variants thereof
54. The composition of paragraph 53, further comprising a pharmaceutically acceptable carrier.
55. The composition of paragraph 53, further comprising a cell culture medium.
56. The composition of any of paragraphs 53-55, wherein at least one cardiac stem cell expresses IGF-1 receptor.
57. The composition of any of paragraphs 53-56, wherein the effective amount of IGF-1 is sufficient to increase proliferation of the cardiac stem cells by at least about 10%, as compared to cardiac stem cells in the absence of IGF-1.
58. The composition of any of paragraphs 53-57, wherein the effective amount of IGF-2 is sufficient to increase expression of at least one marker for myocyte differentiation by at least about 10%, as compared to cardiac stem cells in the absence of IGF-2.
59. The composition of paragraph 58, wherein the marker for myocyte differentiation is selected from the group consisting of: α-sarcomeric actin, connexin-43, Nkx2.5, GATA-4 and MEF2C.
60. The composition of any of paragraphs 53-59, wherein IGF-2 or a variant thereof is added after the cardiac stem cell has been contacted with IGF-1 or a variant thereof.
61. The composition of paragraph 60, wherein the cardiac stem cell has been contacted with IGF-1 for at least about 12 hours.
62. The composition of any of paragraphs 53-61, wherein the cardiac stem cell is isolated from a myocardial tissue of a subject.
63. Use of the composition of paragraph 45 or 53 for administration to a subject in need thereof.
64. The use of paragraph 63, wherein the subject in need thereof has a damaged myocardium.
65. The use of any of paragraphs 63-64, wherein the subject in need thereof is diagnosed with or suffering from a myocardial infarction.
66. The use of any of paragraphs 63-65, wherein the subject in need thereof is diagnosed with or suffering from a heart failure.
67. The use of any of paragraphs 63-66, wherein the subject in need thereof is diagnosed with or suffering from an age-related cardiomyopathy.
68. The use of any of paragraphs 63-67, wherein the subject is a mammal.
69. The use of paragraph 68, wherein the mammal is a human.
70. The use of any of paragraphs 63-69, wherein the composition is administered to an area of a damaged heart tissue.
71. The use of any of paragraphs 63-70, wherein the administration is performed by injection.
72. The use of any of paragraphs 63-71, wherein the administration is performed by a catheter.
73. The use of any of paragraphs 63-72, wherein the administration is intracoronary administration.

EXAMPLES

The examples presented herein relate to methods to identify a human cardiac stem cell (hCSC) subset with high growth reserve, and methods to treat heart diseases, e.g., myocardial infarction, by stimulation of cardiac stem cell (CSCs) with IGF-1 or IGF-2. In one embodiment, the cardiac stem cells are pre-treated with IGF-1 or IGF-2 for enhancing cell proliferation in vitro. In one embodiment, the cardiac stem cells are treated with IGF-2 for enhancing hCSC differentiation to myocyte progeny. Accordingly, the methods, and IGF-2 alone or together with IGF-1, can be used for treatment of heart diseases, such as myocardial infarction. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the paragraphs to the invention, but are rather intended to be exemplary of certain embodiments. Any variations in the exemplified methods which occur to the skilled artisan are intended to fall within the scope of the present invention.

Example 1

IGF-2 Enhances Human Cardiac Stem Cell (hCSCs) Differentiation and Myocardial Regeneration after Infarction The reconstitution of muscle mass by cell implantation after infarction is limited by two factors: number of cells engrafted into the recipient myocardium and modest differentiation of the cardiomyocyte progeny. The IGF system exerts powerful growth promoting and cell survival effects, suggesting that stem cells expressing the IGF-1 receptor (IGF-1R) may be more effective in promoting cardiac repair following ischemic myocardial damage. The IGF system consists of two ligands, IGF-1 and IGF-2, which both activate IGF-1R, although the cellular response to these two ligands may differ significantly. Therefore, hCSCs were isolated from myocardial samples collected from 8 patients. The hCSCs expressed c-kit and were negative for hematopoietic markers including CD34, CD45, CD133, CD105, CD90 and multiple markers of bone marrow cell lineages. They were also negative for cardiac transcription factors (Nkx2.5, MEF2C, GATA4, GATA6, Ets1) and cardiac cytoplasmic/membrane proteins (α-sarcomeric actin, α-smooth muscle actin, vWf, CD31). The presence and absence of IGF-1R was determined at the mRNA and protein level by quantitative Western blotting and immunocytochemistry. Subsequently, two populations of hCSCs were obtained by FACS: IGF-1R$^{POS}$ and IGF-1R$^{NEG}$. In vitro, non-stimulated IGF-1R$^{POS}$-hCSCs had a population doubling time that was 2-fold shorter than in IGF-1R$^{NEG}$-hCSCs. IGF-1 and IGF-2 enhanced further the proliferative response of IGF-1R$^{POS}$-hCSCs due to longer telomeres and higher level of telomerase activity. Additionally, IGF-2 increased dramatically the expression of markers of myocyte differentiation pointing to this ligand as a critical variable for the maturation of the committed myocyte progeny. Based on these findings, it was next sought to assess whether IGF-1R$^{POS}$-hCSCs pre-treated with IGF-2 led to an expansion of the myocyte mass in the acutely infracted heart of immunosuppressed rats. In comparison with IGF-1R$^{POS}$-hCSCs not exposed to IGF-2, growth factor activated IGF-1R$^{POS}$-hCSCs resulted in a larger magnitude of myocardial regeneration mediated by a nearly 2.5-fold significant increase in myocyte volume; the newly formed cardiomyocytes tended to acquire a more mature adult phenotype. These findings, obtained 16 days after coronary occlusion and the delivery of IGF-2 stimulated IGF-1R$^{POS}$-hCSCs, were accompanied by a 10 point increase in ejection fraction, attenuation in ventricular dilation and thickening of the ventricular wall. Thus, activation of IGF-1R$^{POS}$-hCSCs by IGF-2 potentiates cardiac repair and improves the performance of the infracted heart.

Example 2

Dual Role of the IGF System in the Modulation of the Akt-mTOR Pathway in Human Cardiac Stem Cells (hCSCs)

Human cardiac stem cells (hCSCs) were identified to express IGF-1 receptors (IGF-IR) which can be activated by both IGF-1 and IGF-2 ligands. However, IGF-1 promotes hCSC proliferation while IGF-2 favors hCSC commitment and the acquisition of the cardiomyocyte phenotype. It was sought to determine whether the differential response of hCSCs to these growth factors was dictated by distinct downstream effector pathways. As such, the Akt-mTOR signaling mechanism was analyzed in IGF-1R-positive hCSCs exposed in vitro to IGF-1 or IGF-2 for 10, 15 and 30 minutes. With both ligands, IGF-1R underwent a similar degree of autophosphorylation at the three tyrosine residues located in the kinase domain of the receptor. Although total Akt did not differ in hCSCs stimulated with IGF-1 and IGF-2, phosphorylation of Akt at Thr308 and Ser473 showed a distinct temporal pattern of expression. IGF-2 led to a transient increase in the levels of phosphor-Akt which were high at about 10-15 minutes but were significantly decreased at 30 minutes. In contrast, IGF-1 resulted in a stable up-regulation of phospho-Akt that persisted up to about 30 minutes. Phosphorylation of mTOR at Ser2448 was higher in the presence of IGF-1 pointing to a greater ability of mTOR to interact with Rictor and Raptor. Consistently, the mTOR-Rictor complex, TORC1, was more abundant in IGF-1 than in IGF-2 treated hCSCs. However, the up-regulation of Raptor was more pronounced in hCSCs exposed to IGF-2. Collectively, these results indicate that IGF-1 leads to a persistent activation of Akt that may be critical for hCSC replication and survival while IGF-2 may act preferentially on TORC2 which can condition the autocrine release of IGF-2. This process may attenuate IGF-1 function, interfering with cell proliferation and facilitating cell differentiation. In conclusion, the separate function of IGF-1 and IGF-2 on hCSCs can have important implications in the implementation of cell therapy for the failing human heart: autologous hCSCs activated by IGF-1 can be employed to rapidly expand the pool of functionally competent stem cells while IGF-2 can be introduced subsequently to enhance myocyte formation and their acquisition of the adult cell phenotype.

Example 3

Growth Factor Receptor Systems in Human Cardiac Stem Cells (hCSCs)

Because of the multiple variables that interfere with the growth behavior of stem cells in the aging, decompensated heart, it was sought to assess whether specific surface receptors can be employed to distinguish hCSCs with high and low replicative reserve and ability to form myocytes and coronary vessels within a damaged myocardium, e.g., an aging and diseased myocardium. Based on animal models of aging and ischemic heart failure (13-16), the insulin-like growth factor (IGF) system and the renin-angiotensin system (RAS) were characterized in hCSCs to establish whether they can be employed to distinguish pools of primitive cells with different therapeutic value for patients with ventricular dysfunction. Additionally, the effect of IGF-1, IGF-2 and angiotensin II (Ang II) on hCSC division, maturation and death was determined. A series of in vitro and in vivo assays were performed to determine the independent and combined function of IGF-1 receptor (IGF-1R), IGF-2 receptor (IGF-2R) and angiotensin type 1 receptor (AT1R) and their respective ligands in hCSC growth and repair capacity.

Three complementary methodologies were employed to document the presence of three growth factor-receptor systems in c-kit positive hCSCs. The three growth factor-receptor systems were the insulin-like growth factor-1 (IGF-1) system, the insulin-like growth factor-2 (IGF-2) system and the rennin-angiotensin system (RAS). IGF-1-IGF-1R, IGF-2-IGF-2R and RAS were identified in these cells by quantitative real-time polymerase chain reaction (qRT-PCR), FACS analysis and immunocytochemistry. These methods were used to exclude the possibility of protein products derived from uptake of ligands from the circulation, which could otherwise raise question on the origin of IGF-1, IGF-2 and Ang II, and the ability of hCSCs to synthesize these growth factors.

Transcripts for IGF-1, IGF-1R, IGF-2, IGF-2R, angiotensinogen (Aogen), renin, angiotensin-converting enzyme (ACE) and angiotensin type 1 receptor (AT1R) were found in all cases, while angiotensin type 2 receptor (AT2R) mRNA was undetectable (Data not shown). Importantly, IGF-1, IGF-1R, IGF-2, IGF-2R, AT1R and AT2R proteins were expressed in hCSCs. These ligand and receptor epitopes were detected by FACS (Data not shown), and immunolabeling and confocal microscopy (Data not shown). Additionally, Aogen, renin, ACE and angiotensin II (Ang II) were recognized by confocal microscopy in the cytoplasm of hCSCs (Data not shown).

The function of IGF-1 is largely mediated by binding to the receptor tyrosine kinase IGF-1R (17). Alternative splicing occurs at the 5' and 3' ends of the Igf1 gene giving rise to several isoforms. All isoforms produce an identical mature form of IGF-1 that may undergo cleavage with release of the E peptide prior to secretion (18). Although not all E peptides are cleaved prior to the secretion of IGF-1, it is generally believed that mature IGF-1 is the main mediator of the actions of IGF-1 through IGF-1R (19). The Eb-peptide fragments, IBE1 and IBE2, are produced by IGF-1 class B isoforms and stimulate cell growth (18, 19). However, this E peptide extension is unique to the IGF-1 class B. For IGF-1 class A and C, splicing results in a frame shift and a premature termination of translation. Based on qRT-PCR, the predominant IGF-1 isoform in hCSCs and human myocardium was IGF-1A (Data not shown). The role of the short E peptide of IGF-1A has not been characterized. Thus, hCSCs possess three growth factor-receptor systems which may have important implications in defining the biological properties of these human cardiac stem cells.

Example 4

Correlation of Age and Diabetes with Growth Factor Receptor Systems in hCSCs

A cohort of 24 patients affected by chronic coronary artery disease was studied. These patients underwent elective bypass surgery for multi-vessel coronary atherosclerosis and largely preserved cardiac function. Age varied from 48 to 86 years and both genders were represented: 10 women and 14 men. Type 2 diabetes was present in 7 women and 4 men and hypertension in 4 women and 10 men (Data not shown). At surgery, the right atrial appendage was sampled and c-kit-positive hCSCs were isolated and propagated in vitro (Data not shown). Expanded hCSCs, at P4-P5, were characterized by FACS analysis. At these passages, 90±3% hCSCs were c-kit-positive and lineage negative. hCSCs did not express markers of hematopoietic stem cells and bone marrow derived cells. Epitopes of mesenchymal stromal cells were also absent (Data not shown). Moreover, transcription factors specific of myocytes, smooth muscle cells (SMCs) and endothelial cells (ECs) were rarely observed and cytoplasmic and membrane proteins characteristic of cardiac cells were not detected (Data not shown).

Age was found to be the most critical factor associated with changes in the expression of IGF-1R, IGF-2R and AT1R in hCSCs. The percentage of hCSCs positive for IGF-1R decreased with aging while the fraction of cells expressing IGF-2R and AT1R increased (Data not shown). Importantly, a comparable effect of age was observed with respect to the intracellular content of IGF-1, IGF-2 and Ang II (Data not shown). The relatively modest degree of ventricular dysfunction, the duration of coronary artery disease and gender did not correlate with receptor and ligand expression (Data not shown). However, type 2 diabetes led to a further increase in the number of hCSCs positive for AT1R and IGF-2R (Data not shown). Thus, aging up-regulates the RAS and the IGF-2-IGF-2R axis but attenuates the IGF-1-IGF-1R pathway in hCSCs. Diabetes has an additive effect on these cellular properties.

Example 5

Effect of IGFs on hCSC Growth

Auto-phosphorylation of IGF-1R leads to recruitment of the insulin receptor substrate protein (IRS) that upregulates PI3K and Akt. According to its cytoplasmic or nuclear localization, phospho-Akt favors cellular hypertrophy, differentiation or proliferation (20-22). IGF-2 is the predominant form of IGF in humans; it binds to IGF-1R, IGF-2R, and the insulin receptor A isoform (23, 24). Binding of IGF-2 to IGF-2R promotes IGF-2 degradation and prevents its interaction with IGF-1R (25).

To determine the role of IGF-1R and IGF-2R in hCSC growth, cells expressing only one of these two receptors, or both, were sorted by FACS and characterized (Data not shown). Population doubling time (PDT) was shorter in IGF-1R-positive, longer in IGF-2R-positive and intermediate in hCSCs that express both IGF-1R and IGF-2R (IGF-1R-IGF-2R-positive hCSCs) (Data not shown). However, PDT defines the growth kinetics of a cell pool but does not assess the fraction of cycling cells. Thus, the fraction of cycling cells was evaluated by BrdU labeling of hCSCs for a 12 hour period: BrdU was higher in IGF-1R-positive hCSCs with shorter PDT and lower in IGF-2R-positive hCSCs with longer PDT. These results confirm the enhanced proliferation capacity of hCSCs expressing the IGF-1R (Data not shown).

Subsequently, the impact of each ligand, IGF-1 and IGF-2, on hCSC division was assessed. IGF-1 increased the proliferation of hCSCs expressing IGF-1R alone or together with IGF-2R. IGF-2 had similar consequences but of smaller magnitude (Data not shown). Conversely, IGF-1 or IGF-2 failed to enhance proliferation (detected by BrdU labeling) of IGF-2R-positive hCSCs. To verify that the growth-promoting effects of IGF-1 and IGF-2 on hCSCs were mediated by activation of IGF-1R, these experiments were repeated in the presence of an IGF-1R blocking antibody. Under this condition, hCSC division was largely inhibited (Data not shown). Thus, IGF-1 and IGF-2 promote hCSC division by activating IGF-1R while IGF-2R has no influence on hCSC replication.

Example 6

Effect of IGFs on hCSC Differentiation

In several cell systems, IGF-1 and IGF-2 promote cell differentiation rather than cell proliferation (17). Although these opposite processes of cell growth may be cell context dependent (26), whether IGF-1 and IGF-2 regulate exclusively hCSC division or also have the ability to induce the commitment of hCSCs to the myocyte lineage is presently unknown. Additionally, it is not known whether the response of hCSCs to IGF-1 and/or IGF-2 is time dependent.

To investigate the time dependency of hCSCs in response to IGFs, lineage negative hCSCs were exposed to IGF-1 or IGF-2 for 12, 24 and 48 hours. The expression of the myocyte transcription factors GATA4 and Nkx2.5, and the contractile protein α-sarcomeric actin (α-SA) was determined by qRT-PCR and immunolabeling and confocal microscopy. In IGF-1R-positive hCSCs, the quantity of mRNA for GATA4, Nkx2.5 and α-SA increased markedly 24 hours after IGF-2 stimulation; IGF-1 had much smaller effects on hCSC differentiation (Data not shown).

At the protein level, the percentage of hCSCs positive for GATA4, Nkx2.5 and α-SA in the presence of IGF-2 increased progressively from 12 to 24 and 48 hours. Similar to the mRNA results obtained by qRT-PCR, the impact of IGF-1 on IGF-1R-positive hCSCs and myocyte commitment was less pronounced than that of IGF-2 (Data not shown). Importantly, the differentiating response was observed only at 48 hours, a time point characterized by a marked increase in IGF-2 in the medium (Data not shown), mediated by the synthesis and secretion of this growth factor by IGF-1R activation of hCSCs. Moreover, the differentiation of hCSCs into cardiomyocytes by IGF-1 and IGF-2 stimulation was rather modest when hCSCs were positive for both IGF-1R and IGF-2R, or positive only for IGF-2R (Data not shown). Accordingly, the early activation of IGF-1R by IGF-1 or IGF-2 and cell multiplication (Data not shown) may be followed by hCSC differentiation.

The critical role of IGF-2-mediated activation of IGF-1R in hCSC commitment to the myocyte lineage was further assessed. Blockade of this effector pathway by IGF-1R antibodies largely preserved the undifferentiated state of hCSCs (Data not shown). Therefore, the transition from hCSC replication to lineage specification may involve the autocrine/paracrine release of IGF-2 from IGF-1R-positive hCSCs following their prolonged stimulation by IGF-1.

Example 7

IGFs and Physiological Competence of hCSC-Derived Cardiomyocytes

To determine whether myocytes derived from hCSCs exposed to sustained stimulation with IGF-2 or IGF-1 were functionally-competent, some additional molecular properties were defined and complemented with the analysis of their electrical and mechanical behavior. Comparable phenotypes were observed in myocytes derived from hCSCs stimulated by IGF-2 or IGF-1, but the degree of differentiation was higher in IGF-2-stimulated hCSCs. Differentiating myocytes expressed transcripts of myosin light chain 2v, L-type $Ca^+$ channels, $K^+$ channels Kir2.1 and the α-subunit of voltage gated $Na^+$ channels type V (Data not shown). Ryanodine receptor mRNA level was low but the intracellular $Ca^+$ concentration increased in the presence of caffeine, pointing to the functionality of this receptor in developing myocytes (Data not shown). Following stimulation at 1 Hz, cells showed prolonged action potentials and contractile activity (Data not shown). Importantly, myofibrillar structures with sarcomere striations were observed in the subsarcolemmal region (Data not shown). Thus, IGF-2 and IGF-1 are important modulators of hCSCs growth and differentiation, and IGF-2 induces higher degree of hCSC differentiation.

Example 8

Effect of IGFs on hCSC Death

Although the anti-apoptotic effects of IGF-1 on cardiac stem cells have been reported experimentally (27), the role of IGF-2 in hCSC survival or death has not been studied. Yet this is a relevant question because IGF-2 is important in the maturation of myocytes and it is the predominant form of IGFs in humans (23).

To assess the effect of IGF-2 on hCSC apoptosis or cell death, Ang II was employed as the trigger for apoptotic cell death (15, 28). In the absence of Ang II, the baseline level of apoptosis was modest and similar in IGF-1R-positive, IGF-2R-positive and IGF-1R-IGF-2R-positive hCSCs. The presence of Ang II at $10^{-9}$M increased apoptosis in all three hCSC subsets, but predominantly in IGF-2R-positive and IGF-1R-IGF-2R-positive hCSCs. The addition of IGF-1 attenuated apoptosis in IGF-1R-positive hCSCs only while IGF-2 increased death of hCSCs expressing IGF-2R alone or together with IGF-1R. However, the highest value was detected in IGF-2R-positive hCSCs (Data not shown). Importantly, the differential response of these three hCSC subsets to Ang II reflected comparable differences in the level of AT1R expression in IGF-1R-positive, IGF-2R-positive and IGF-1R-IGF-2R-positive hCSCs (Data not shown). IGF-2 alone increased the degree of apoptosis in IGF-2R-positive hCSCs and this response was inhibited in the presence of IGF-2R blocking antibodies (Data not shown). Thus, activation of IGF-2R by IGF-2 triggers apoptosis opposing the survival effects promoted by IGF-1.

Example 9

IGFs, RAS and the Telomere-Telomerase Axis in hCSCs

The growth or expansion of stem cells is regulated by the length of their telomeres and the level of telomerase activity which restores in part the telomere DNA lost following each cell division (29). These two variables of stem cell growth or expansion were measured in a subset of 12 patients, from 48 to 86 years of age, to determine the replication reserve of IGF-1R-positive, IGF-2R-positive and AT1R-positive hCSCs. This information is critical for identifying a hCSC compartment which possesses the highest potential for myocardial regeneration and recovery of function of a diseased heart.

In all 12 cases, IGF-1R-positive hCSCs had longer telomeres than IGF-2R-positive cells, while AT1R-positive hCSCs had the shortest telomeres (Data not shown). Age did not affect telomere length in any of these three hCSC groups, indicating that a pool of hCSCs with essentially normal telomere length, 9-10 kbp, can be present in a human heart at 46 as well as at 86 years of age. Although aging increased the pool of hCSCs with short telomeres, i.e., AT1R-positive hCSCs, and decreased the pool of hCSCs with long telomeres, i.e., IGF-1R-positive hCSCs (Data not shown), age did not deplete the compartment of highly functional resident stem cells, suggesting that the old heart retains a considerable growth reserve for cell turnover and tissue regeneration.

Measurements of telomerase activity in these three hCSC groups from each of the 12 cases showed a comparable behavior (Data not shown). IGF-1R-positive hCSCs had the highest telomerase activity while IGF-2R-positive and AT1R-positive hCSCs showed a reduced activity, confirming that IGF-1R-positive hCSCs constitute the most powerful hCSC subset for cell therapy of an old decompensated heart. This notion is consistent with the expression of the senescence-associated protein p16$^{INK4a}$ in hCSCs which was significantly higher in IGF-2R-positive and AT1R-positive hCSCs than in IGF-1R-positive hCSCs (Data not shown). Collectively, these findings suggest that a highly enriched pool of IGF-1R-positive hCSCs should have a higher regeneration potential than a non-selected hCSC population. Additionally, stimulation of IGF-1R-positive hCSCs with IGF-2 may enhance their in vivo differentiation into mature cardiomyocytes, offering therapeutic options for the repair process of an infarcted heart.

Example 10

Myocardial Regeneration after Infarction

To determine the therapeutic efficacy of unselected hCSCs (Un-hCSCs), IGF-1R-positive hCSCs (IGF-1R-hCSCs), and IGF-2-activated IGF-1R-positive hCSCs (Ac-IGF-1R-hCSCs) in myocardial regeneration, these cells were infected with a lentivirus carrying EGFP (enhanced green fluorescent protein) and delivered intramyocardially shortly after coronary artery ligation in immunosuppressed rats. Infarcted immunosuppressed rats injected with saline were used as controls. In the three groups of hCSC-treated animals, large areas of infarcted myocardium were replaced by newly-formed EGFP-positive human myocytes and coronary vessels 10 days after surgery (Data not shown). Foci of tissue regeneration were not observed in untreated infarcts, suggesting that myocyte and vessel formation was restricted to the surviving myocardium without invasion into the scarred region of the wall (8, 14, 16, 30).

Infarct size, measured by the number of rat myocytes lost as a result of permanent coronary occlusion, involved nearly 70% of the cells of the left ventricle (Data not shown). In all the three groups of hCSC-treated animals, the band of newly-formed human tissue was distributed in the midportion of the infarct and only occasionally reached the epi- or endomyocardium. The human origin of the regenerated myocytes was confirmed by the detection of human DNA sequences with an Alu probe, together with the identification of human X-chromosomes by Q-FISH and the expression of human troponin I (Data not shown). Accordingly, the regenerated human coronary arterioles and capillaries were Alu-positive and carried human X-chromosomes (Data not shown). In all the three groups of hCSC-treated animals, the newly-formed packed myocytes occupied ~84% of the regenerated tissue while arterioles and capillaries accounted for ~8%.

The human myocardium comprised 7, 12 and 15 mm$^3$ following treatment with Un-hCSCs, IGF-1R-hCSCs and Ac-IGF-1R-hCSCs, respectively (Data not shown), indicating that the unselected pool of hCSCs was associated with a smaller degree of tissue reconstitution after infarction. The increased recovery in myocardial mass in the other two cases resulted in an attenuation of ventricular dilation and thinning of the wall in the spared and infarcted region of the left ventricle (LV) (Data not shown). Relevant differences were also found in the magnitude and characteristics of the human myocardium formed by IGF-1R-hCSCs and Ac-IGF-1R-hCSCs. The latter cell population (Ac-IGF-1R-hCSCs) led to a 30% higher degree of tissue regeneration which was the product of a 2.7-fold larger average myocyte volume and a 40% lower aggregate number of myocytes (Data not shown). The prevailing hypertrophic response observed with Ac-IGF-1R-hCSCs was consistent with the in vitro findings and the relatively low level of myocyte replication measured by Ki67 in the regenerated myocardium (Data not shown). Moreover, the number of capillary profiles per mm$^2$ of myocardium was higher in these hearts treated with Ac-IGF-1R-hCSCs, reflecting a commensurate magnitude of vascularization dictated by the larger myocyte cross-sectional area (Data not shown). These positive effects were coupled with a reduced hypertrophic reaction of the spared rat cardiomyocytes (Data not shown) and less negative LV remodeling (Data not shown).

Functionally, myocardial regeneration was characterized by the reappearance of contraction in the infarcted region of the LV wall which was more pronounced following the delivery of Ac-IGF-1R-hCSCs (Data not shown). In addition, these Ac-IGF-1R-hCSCs led to a better improvement of LV systolic pressure and positive and negative dP/dt (Data not shown). Additionally, calculated diastolic wall stress was significantly decreased in these animals (Data not shown). Thus, activation by IGF-2 of hCSCs expressing only IGF-1R provides a remarkable recovery in the structure and function of the infarcted heart.

Discussion

Examples 3-10 indicate that isolation and expansion of c-kit-positive hCSCs from small samples of human myocardium yields a heterogeneous cell population composed of stem cell subsets with considerably different growth reserve in vitro and in vivo. The stem cell antigen c-kit is expressed in a population of hematopoietic stem cells that are capable of differentiating into cardiomyocytes and coronary vessels, replacing in part large myocardial infarcts with restoration of ventricular performance (1). Similarly, the c-kit receptor tyrosine kinase identifies a pool of cardiac cells which reside in niches (31), possess the properties of stem cells and regenerate in vivo infarcted tissue with contracting myocardium (8, 32). However, presented herein show that the association of c-kit with distinct proteins on the membrane of hCSCs conditions functional differences within an apparently uniform cell compartment. The behavior of hCSCs is dictated by a specific surface phenotype which permits the selective isolation of young highly dividing hCSCs from the pool of c-kit-positive cells. Different membrane receptors affect the phenotypic plasticity of hCSCs and their ability to compensate myocyte loss by forming new efficiently contracting parenchymal cells.

Aging progressively decreases the compartment of hCSCs with high regenerative potential and progressively increases the pool of stem cells with minimal or no ability to divide and acquire cardiac cell lineages. The loss of hCSC function with aging is mediated partly by an imbalance between factors promoting growth and survival, and factors enhancing oxidative stress, telomere attrition and apoptosis. Three growth-factor receptor systems seem to have a critical role in hCSC replication, differentiation, senescence and death: IGF-1-IGF-1R, IGF-2-IGF-2R and RAS. The IGF-1-IGF-1R induces hCSC division, up-regulates telomerase activity, maintains telomere length, hinders replicative senescence and preserves the population of functionally-competent CSCs in animals (13) and, as demonstrated herein, in humans. The expression of IGF-1R and the synthesis of IGF-1 are attenuated in aging hCSCs, possibly diminishing the ability of IGF-1 to activate cell proliferation and interfere with oxidative damage and telomeric shortening (33).

In progenitor cells, IGF-1 is generally linked to the protection of the primitive phenotype (34) while IGF-2 induces the acquisition of the committed state, a phenomenon that has been herein identified in hCSCs. The presence of IGF-2 conditions the osteogenic differentiation of mesenchymal stromal cells (35) and the formation of skeletal myoblasts by satellite cells (36). The function of IGF-1R-positive hCSCs is regulated by both IGF-1 and IGF-2 which exert opposite effects on the fate of these cells. Importantly, cardiomyocytes and fibroblasts surrounding hCSCs have the ability to secrete the IGF-1 and IGF-2 ligand (37, 38), suggesting that a cross-talk occurs within the cardiac niches where myocytes and fibroblasts function as supporting cells (31). These cells may dictate the developmental decision of hCSCs according to the needs of the organ. Based on the human data presented herein and previous findings in animals (14, 15, 30), IGF-1 may activate IGF-1R-positive hCSCs which possess high telomerase activity and rather intact telomeres, favoring their migration out of the niche area to regions of myocyte replacement. Defects in telomerase activity and telomere length oppose lodging and motility of progenitor cells in the skin (39) and in the heart (15). Additionally, IGF-2, formed via an autocrine/paracrine mechanism (40, 41), may promote the transition of amplifying cells to a class of myocytes with a more mature phenotype, structurally and mechanically.

Consistent with these observations, skeletal muscle differentiation is strictly dependent on an autocrine loop initiated by the muscle secretion of IGF-2 that binds to IGF-1R in myoblasts (42). This effector pathway targets transcriptional regulators of MyoD and the myogenin promoter (43, 44). A similar mechanism appears to mediate cardiomyocyte differentiation, although the signaling cascade located downstream IGF-1R in hCSCs remains to be determined. Thus, the finding that hCSCs expressing only IGF-1R synthesize both IGF-1 and IGF-2, which are potent modulators of stem cell replication, stem cell commitment to the myocyte lineage and myocyte differentiation, points to this hCSC subset expressing only IGF-1R as the ideal candidate cell for the management of human heart failure.

The main function of IGF-2R is related to the clearance of IGF-2. Binding of IGF-2 to IGF-2R limits ligand bioavailability, inducing IGF-2 degradation and, thereby, preventing its interaction with IGF-1R (25). Presented herein is a novel function of IGF-2: ligand binding to IGF-2R promotes apoptosis of hCSCs and enhances the effects of Ang II on cell death. The high level of AT1R expression in IGF-2R-positive hCSCs defines the surface phenotype of senescent cells greatly prone to apoptotic death. Under conditions in which hCSC survival is essential for the well-being of the organ and organism, the up-regulation of death genes appears to be a paradoxical response. However, preservation of the steady state may conform to an intrinsic mechanism aiming at the maintenance of a constant number of functionally-competent hCSCs within the myocardial niches. Apoptosis of hCSCs may be regarded as a biological adaptation that removes unwanted old cells and concurrently triggers replication of young hCSCs and their commitment to the myocyte lineage.

IGFs are bound to IGF-binding proteins (IGFBPs), which modulate IGF ligand-receptor interactions and, thereby, their function. IGFPBs prolong the half-life of IGFs, but this process can result in the inhibition or stimulation of IGF-1R and IGF-2R pathway (45). Although the importance of IGFBPs is largely unknown, these proteins add a level of complexity to the study of IGFs. Recently, IGFBP-4 has been shown to enhance cardiomyocyte differentiation in vitro while its deletion attenuates cardiomyogenesis in vitro and in vivo (46). This role of IGFBP-4 is independent from its IGF-binding activity and is mediated by its direct interaction with Wnt receptors.

The finding that a local RAS is present in hCSCs and the formation of Ang II, together with the expression of AT1R, increases with age in hCSCs provides evidence in favor of the role of this octapeptide in hCSC senescence and death. Ang II may contribute to the age-dependent accumulation of oxidative damage in the heart (47). Inhibition of Ang II positively interferes with heart failure and prolongs life in humans (48). Ang II generates reactive oxygen species (ROS) and the most prominent form of DNA damage induced by free radicals is 8-OH-dG. In the presence of Ang II, the level of 8-OH-dG increases more in old than in young progenitor cells (15). 8-OH-dG accumulates at the GGG triplets of telomeres resulting in telomeric shortening and uncapping (49). Loss of telomere integrity is the major determinant of cellular senescence and death. Conversely, IGF-1 interferes with ROS generation (47), decreases oxidative stress with age (13), and can repair DNA damage by homologous recombination (50). Cardiac restricted overexpression of IGF-1 delays the aging myopathy and the manifestations of heart failure in transgenic mice (13). Thus, changes in the proportion of these growth factor receptor systems in hCSCs condition their growth reserve and potential therapeutic efficacy, a phenomenon demonstrated here after infarction and the delivery of hCSC subsets.

In summary, c-kit-positive-hCSCs comprise a heterogeneous population of hCSCs with different potentials of growth reserve. The expression of IGF-1R in hCSCs recognized a young cell phenotype defined by long telomeres, high telomerase activity, enhanced cell proliferation and attenuated apoptosis. In addition to IGF-1, IGF-1R-positive-hCSCs secreted IGF-2 that promoted myocyte differentiation. Conversely, the presence of IGF-2R and AT1R, in the absence of IGF-1R, identified senescent hCSCs with impaired growth reserve and increased susceptibility to apoptosis. IGF-1R-positive-hCSCs improved cardiomyogenesis and vasculogenesis. Pretreatment of IGF-1R-positive-hCSCs with IGF-2 resulted in the formation of more mature myocytes and superior recovery of ventricular mass and function. hCSCs expressing only IGF-1R synthesize both IGF-1 and IGF-2, which are potent modulators of stem cell replication, commitment to the myocyte lineage and myocyte differentiation, points to this hCSC subset as the ideal candidate cell for the management of human heart failure. Accordingly, the results presented herein suggest that the clinical implementation of autologous hCSCs in patients with acute and chronic ischemic cardiomyopathy necessitates a rather sophisticated approach which involves the characterization of the molecular signature of the cells to be delivered. Although extremely large numbers of different classes of bone marrow progenitor cells are currently being administered to patients, and hCSCs are now entering the scene of cell therapy for the decompensated heart, a careful analysis of the phenotypic properties of the cells to be used has to be considered. The quality of the cells can be the critical factor for successful clinical outcome rather than cell number.

REFERENCES

1. Orlic D, Kaj stura J, Chimenti S, Jakoniuk I, Anderson S M, Li B, Pickel J, McKay R, Nadal-Ginard B, Bodine D M, Leri A, Anversa P. Bone marrow cells regenerate infarcted myocardium. Nature. 2001; 410:701-705.
2. Murasawa S, Kawamoto A, Horii M, Nakamori S, Asahara T. Niche-dependent translineage commitment of endothelial progenitor cells, not cell fusion in general, into myocardial lineage cells. Arterioscler Thromb Vasc Biol. 2005; 25:1388-1394.
3. Losordo D W, Schatz R A, White C J, Udelson J E, Veereshwarayya V, Durgin M, Poh K K, Weinstein R, Kearney M, Chaudhry M, Burg A, Eaton L, Heyd L, Thorne T, Shturman L, Hoffmeister P, Story K, Zak V, Dowling D, Traverse J H, Olson R E, Flanagan J, Sodano D, Murayama T, Kawamoto A, Kusano K F, Wollins J, Welt F, Shah P, Soukas P, Asahara T, Henry T D. Intramyocardial transplantation of autologous CD34+ stem cells for intractable angina: a phase I/IIa double-blind, randomized controlled trial. Circulation. 2007; 115: 3165-3172.
4. Schächinger V, Erbs S, Elsässer A, Haberbosch W, Hambrecht R, Hölschermann H, Yu J, Corti R, Mathey D G, Hamm C W, Süselbeck T, Assmus B, Tonn T, Dimmeler S, Zeiher A M; REPAIR-AMI Investigators. Intracoronary bone marrow-derived progenitor cells in acute myocardial infarction. N Engl J Med. 2006; 355:1210-1221.
5. Kawamoto A, Iwasaki H, Kusano K, Murayama T, Oyamada A, Silver M, Hulbert C, Gavin M, Hanley A, Ma H, Kearney M, Zak V, Asahara T, Losordo D W. CD34-positive cells exhibit increased potency and safety for therapeutic neovascularization after myocardial infarction compared with total mononuclear cells. Circulation. 2006; 114:2163-2169.
6. Hare J M, Traverse J H, Henry T D, Dib N, Strumpf R K, Schulman S P, Gerstenblith G, DeMaria A N, Denktas A E, Gammon R S, Hermiller J B Jr, Reisman M A, Schaer G L, Sherman W. A randomized, double-blind, placebo-controlled, dose-escalation study of intravenous adult human mesenchymal stem cells (prochymal) after acute myocardial infarction. J Am Coll Cardiol. 2009; 54:2277-2286.
7. Smith R R, Barile L, Cho H C, Leppo M K, Hare J M, Messina E, Giacomello A, Abraham M R, Marbán E. Regenerative potential of cardiosphere-derived cells expanded from percutaneous endomyocardial biopsy specimens. Circulation. 2007; 115:896-908.
8. Bearzi C, Rota M, Hosoda T, Tillmanns J, Nascimbene A, De Angelis A, Yasuzawa-Amano S, Trofimova I, Siggins R W, Lecapitaine N, Cascapera S, Beltrami A P, DAlessandro D A, Zias E, Quaini F, Urbanek K, Michler R E, Bolli R, Kaj stura J, Leri A, Anversa P. Human cardiac stem cells. Proc Natl Acad Sci USA. 2007; 104:14068-14073.
9. Itzhaki-Alfia A, Leor J, Raanani E, Sternik L, Spiegelstein D, Netser S, Holbova R, Pevsner-Fischer M, Lavee J, Barbash I M. Patient characteristics and cell source determine the number of isolated human cardiac stem cells. Circulation. 2009; 120:2559-2566.
10. Chimenti C, Kajstura J, Torella D, Urbanek K, Heleniak H, Colussi C, Di Meglio F, Nadal-Ginard B, Frustaci A, Leri A, Maseri A, Anversa P. Senescence and death of primitive cells and myocytes lead to premature cardiac aging and heart failure. Circ Res. 2003; 93:604-613.
11. Urbanek K, Quaini F, Tasca G, Torella D, Castaldo C, Nadal-Ginard B, Leri A, Kaj stura J, Quaini E, Anversa P. Intense myocyte formation from cardiac stem cells in human cardiac hypertrophy. Proc Natl Acad Sci USA. 2003; 100:10440-10445.
12. Urbanek K, Torella D, Sheikh F, De Angelis A, Nurzynska D, Silvestri F, Beltrami C A, Bussani R, Beltrami A P, Quaini F, Bolli R, Leri A, Kaj stura J, Anversa P. Myocardial regeneration by activation of multipotent cardiac stem cells in ischemic heart failure. Proc Natl Acad Sci USA. 2005; 102:8692-8697.
13. Torella D, Rota M, Nurzynska D, Musso E, Monsen A, Shiraishi I, Zias E, Walsh K, Rosenzweig A, Sussman M A, Urbanek K, Nadal-Ginard B, Kaj stura J, Anversa P, Leri A. Cardiac stem cell and myocyte aging, heart failure, and insulin-like growth factor-1 overexpression. Circ Res. 2004; 94:514-524.
14. Urbanek K, Rota M, Cascapera S, Bearzi C, Nascimbene A, De Angelis A, Hosoda T, Chimenti S, Baker M, Limana F, Nurzynska D, Torella D, Rotatori F, Rastaldo R, Musso E, Quaini F, Leri A, Kajstura J, Anversa P. Cardiac stem cells possess growth factor-receptor systems that after activation regenerate the infarcted myocardium, improving ventricular function and long-term survival. Circ Res. 2005; 97:663-673.
15. Gonzalez A, Rota M, Nurzynska D, Misao Y, Tillmanns J, Ojaimi C, Padin-Iruegas M E, Müller P, Esposito G, Bearzi C, Vitale S, Dawn B, Sanganalmath S K, Baker M, Hintze T H, Bolli R, Urbanek K, Hosoda T, Anversa P, Kaj stura J, Leri A. Activation of cardiac stem cells reverses the failing heart senescent phenotype and prolongs lifespan. Circ Res. 2008; 102:597-606.
16. Rota M, Padin-Iruegas M E, Misao Y, De Angelis A, Maestroni S, Ferreira-Martins J, Fiumana E, Rastaldo R, Arcarese M L, Mitchell T S, Boni A, Bolli R, Urbanek K, Hosoda T, Anversa P, Leri A, Kaj stura J. Local activation or implantation of cardiac stem cells rescues scarred infarcted myocardium improving cardiac function. Circ Res. 2008; 103:107-116.
17. Baserga R. The contradictions of the insulin-like growth factor 1 receptor. Oncogene. 2000; 19:5574-5581.
18. Favelyukis S, Till J H, Hubbard S R, Miller W T. Structure and autoregulation of the insulin-line growth factor 1 receptor kinase. Nat Struct Biol. 2001; 8:1058-1063.
19. Li W, Miller W T. Role of the activation loop tyrosines in regulation of the insulin-like growth factor 1 receptor-tyrosine kinase. J Biol Chem. 2006; 281:23785-23791.
20. Shiraishi I, Melendez J, Ahn Y, Skavdahl M, Murphy E, Welch S, Schaefer E, Walsh K, Rosenzweig A, Torella D, Nurzynska D, Kajstura J, Leri A, Anversa P, Sussman M A. Nuclear targeting of Akt enhances kinase activity and survival of cardiomyocytes. Circ Res. 2004; 94:884-891.
21. Nagoshi T, Matsui T, Aoyama T, Leri A, Anversa P, Li L, Ogawa W, Del Monte F, Gwathmey J K, Grazette L, Hemmings B A, Kass D A, Champion H C, Rosenzweig A. PI3K rescues the detrimental effects of chronic Akt activation in the heart during ischemia/reperfusion injury. J Clin Invest. 2005; 115:2128-2138.
22. Walsh K. Akt signaling and growth of the heart. Circulation. 2006; 113:2032-2034.
23. Baker J, Liu J P, Robertson E J, Efstratiadis A. Role of insulin-like growth factors in embryonic and postnatal growth. Cell. 1993; 75:73-82.
24. Denley A, Bonython E R, Booker G W, Cosgrove L J, Forbes B E, Ward C W, Wallace J C. Structural determinants for high-affinity binding of insulin-like growth factor II to insulin receptor (IR)-A, the exon 11 minus isoform of the IR. Mol Endocrinol. 2004; 18:2502-2512.
25. Ghosh P, Dahms N M, Kornfeld S. Mannose 6-phosphate receptors: new twists in the tale. Nat Rev Mol Cell Biol. 2003; 4:202-212.
26. Petley T, Graff K, Jiang W, Yang H, Florini J. Variation among cell types in the signaling pathways by which IGF-I stimulates specific cellular responses. Horm Metab Res. 1999; 31:70-76.
27. Miyamoto S, Rubio M, Sussman M A. Nuclear and mitochondrial signalling Akts in cardiomyocytes. Cardiovasc Res. 2009; 82:272-285.
28. Rota M, LeCapitaine N, Hosoda T, Boni A, De Angelis A, Padin-Iruegas M E, Esposito G, Vitale S, Urbanek K, Casarsa C, Giorgio M, LUscher T F, Pelicci P G, Anversa P, Leri A, Kaj stura J. Diabetes promotes cardiac stem cell aging and heart failure, which are prevented by deletion of the p66shc gene. Circ Res. 2006; 99:42-52.
29. Chan S W, Blackburn E H. New ways not to make ends meet: telomerase, DNA damage proteins and heterochromatin. Oncogene. 2002; 21:553-563.
30. Padin-Iruegas M E, Misao Y, Davis M E, Segers V F, Esposito G, Tokunou T, Urbanek K, Hosoda T, Rota M, Anversa P, Leri A, Lee R T, Kajstura J. Cardiac stem cells and biotinylated insulin-like growth factor-1 nanofibers improve endogenous and exogenous myocardial regeneration after infarction. Circulation. 2009; 120:876-887.
31. Urbanek K, Cesselli D, Rota M, Nascimbene A, De Angelis A, Hosoda T, Bearzi C, Boni A, Bolli R, Kajstura J, Anversa P, Leri A. Stem cell niches in the adult mouse heart. Proc Natl Acad Sci USA. 2006; 103:9226-9231.
32. Beltrami A P, Barlucchi L, Torella D, Baker M, Limana F, Chimenti S, Kasahara H, Rota M, Musso E, Urbanek K, Leri A, Kajstura J, Nadal-Ginard B, Anversa P. Adult cardiac stem cells are multipotent and support myocardial regeneration. Cell. 2003; 114:763-776.
33. Kenyon C. The plasticity of aging: insights from long-lived mutants. Cell. 2005; 120:449-460.
34. Ye P, D'Ercole A J. Insulin-like growth factor actions during development of neural stem cells and progenitors in the central nervous system. J Neurosci Res. 2006; 83:1-6.
35. Chen L, Jiang W, Huang J, He B C, Zuo G W, Zhang W, Luo Q, Shi Q, Zhang B Q, Wagner E R, Luo J, Tang M, Wietholt C, Luo X, Bi Y, Su Y, Liu B, Kim S H, He C J, Hu Y, Shen J, Rastegar F, Huang E, Gao Y, Gao J L, Zhou J Z, Reid R R, Luu H H, Haydon R C, He T C, Deng Z L. Insulin-like growth factor 2 (IGF2) potentiates BMP9-induced osteogenic differentiation and bone formation. J Bone Miner Res. 2010; In press
36. Roel W, Broek T, Grefte S, Johannes W, Von den Hoff J W. Regulatory factors and cell populations involved in skeletal muscle regeneration. Journal of Cellular Physiology. 2010; 224:7-16.
37. Hu B S, Landeen L K, Aroonsakool N, Giles W R. An analysis of the effects of stretch on IGF-I secretion from rat ventricular fibroblasts. Am J Physiol Heart Circ Physiol. 2007; 293:H677-H683.

38. Blaauw E, van Nieuwenhoven F A, Willemsen P, Delhaas T, Prinzen F W, Snoeckx L H, van Bilsen M, van der Vusse G J. Stretch-induced hypertrophy of isolated adult rabbit cardiomyocytes. Am J Physiol Heart Circ Physiol. 2010; 299:H780-H787.
39. Flores I, Cayuela M L, Blasco M A. Effects of telomerase and telomere length on epidermal stem cell behavior. Science. 2005; 309:1253-1256.
40. Rosenthal S M, Brunetti A, Brown E J, Mamula P W, Goldfine I D. Regulation of insulin-like growth factor (IGF) I receptor expression during muscle cell differentiation. Potential autocrine role of IGF-II. J Clin Invest. 1991; 87:1212-1219.
41. Rosen K M, Wentworth B M, Rosenthal N, Villa-Komaroff L. Specific, temporally regulated expression of the insulin-like growth factor II gene during muscle cell differentiation. Endocrinology. 1993; 133:474-481.
42. Philippou A, Halapas A, Maridaki M, Koutsilieris M. Type I insulin-like growth factor receptor signaling in skeletal muscle regeneration and hypertrophy. J Muscuoskelet Neuronal Interact. 2007; 7:208-218.
43. Wilson E M, Rotwein P. Control of MyoD function during initiation of muscle differentiation by an autocrine signaling pathway activated by insulin-like growth factor-II. J Biol Chem. 2006; 281:29962-29971.
44. Erbay E, Park I H, Nuzzi P D, Schoenherr C J, Chen J. IGF-II transcription in skeletal myogenesis is controlled by mTOR and nutrients. J Cell Biol. 2003; 163:931-936.
45. Le Roith D. Regulation of proliferation and apoptosis by the insulin-like growth factor I receptor. Growth Horm IGF Res. 2000; 10 Suppl A:S12-S13.
46. Zhu W, Shiojima I, Ito Y, Li Z, Ikeda H, Yoshida M, Naito A T, Nishi J, Ueno H, Umezawa A, Minamino T, Nagai T, Kikuchi A, Asashima M, Komuro I. IGFBP-4 is an inhibitor of canonical Wnt signalling required for cardiogenesis. Nature. 2008; 454:345-349.
47. Kajstura J, Fiordaliso F, Andreoli A M, Li B, Chimenti S, Medow M S, Limana F, Nadal-Ginard B, Leri A, Anversa P. IGF-1 overexpression inhibits the development of diabetic cardiomyopathy and angiotensin II-mediated oxidative stress. Diabetes. 2001; 50:1414-1424.
48. O'Meara E, Clayton T, McEntegart M B, McMurray J J V, Pina I L, Granger C B, Ostergren J, Michelson E L, Solomon S D, Pocock S, Yusuf S, Swedberg K, Pfeffer M A, CHARM Investigators. Sex differences in clinical characteristics and prognosis in a broad spectrum of patients with heart failure. Circulation. 2007; 115:3111-3120.
49. Kawanishi S, Oikawa S. Mechanism of telomere shortening by oxidative stress. Ann NY Acad Sci. 2004; 1019:278-284.
50. Yang S, Chintapalli J, Sodagum L, Baskin S, Malhotra A, Reiss K, Meggs L G. Activated IGF-1R inhibits hyperglycemia-induced DNA damage and promotes DNA repair by homologous recombination. Am J Physiol Renal Physiol. 2005; 289:F1144-F1152.

| SEQUENCES | | |
|---|---|---|
| 1 | MGKISSLPTQ LFKCCFCDFL KVKMHTMSSS HLFYLALCLL TFTSSATAGP ETLCGAELVD | |
| 61 | ALQFVCGDRG FYFNKPTGYG SSSRRAPQTG IVDECCFRSC DLRRLEMYCA PLKPAKSARS | |
| 121 | VRAQRHTDMP KTQKYQPPST NKNTKSQRRK GSTFEERK (SEQ ID NO: 1) | |
| 1 | MITPTVKMHT MSSSHLFYLA LCLLTFTSSA TAGPETLCGA ELVDALQFVC GDRGFYFNKP | |
| 61 | TGYGSSSRRA PQTGIVDECC FRSCDLRRLE MYCAPLKPAK SARSVRAQRH TDMPKTQKEV | |
| 121 | HLKNASRGSA GNKNYRM (SEQ ID NO: 2) | |
| 1 | MGKISSLPTQ LFKCCFCDFL KVKMHTMSSS HLFYLALCLL TFTSSATAGP ETLCGAELVD | |
| 61 | ALQFVCGDRG FYFNKPTGYG SSSRRAPQTG IVDECCFRSC DLRRLEMYCA PLKPAKSARS | |
| 121 | VRAQRHTDMP KTQKYQPPST NKNTKSQRRK GWPKTHPGGE QKEGTEASLQ IRGKKKEQRR | |
| 181 | EIGSRNAECR GKKGK (SEQ ID NO: 3) | |
| 1 | MGKISSLPTQ LFKCCFCDFL KVKMHTMSSS HLFYLALCLL TFTSSATAGP ETLCGAELVD | |
| 61 | ALQFVCGDRG FYFNKPTGYG SSSRRAPQTG IVDECCFRSC DLRRLEMYCA PLKPAKSARS | |
| 121 | VRAQRHTDMP KTQKEVHLKN ASRGSAGNKN YRM (SEQ ID NO: 4) | |
| 1 | MGIPMGKSML VLLTFLAFAS CCIAAYRPSE TLCGGELVDT LQFVCGDRGF YFSRPASRVS | |
| 61 | RRSRGIVEEC CFRSCDLALL ETYCATPAKS ERDVSTPPTV LPDNFPRYPV GKFFQYDTWK | |
| 121 | QSTQRLRRGL PALLRARRGH VLAKELEAFR EAKRHRPLIA LPTQDPAHGG APPEMASNRK (SEQ ID NO: 5) | |
| 1 | MGIPMGKSML VLLTFLAFAS CCIAAYRPSE TLCGGELVDT LQFVCGDRGF YFSRPASRVS | |
| 61 | RRSRGIVEEC CFRSCDLALL ETYCATPAKS ERDVSTPPTV LPDNFPRYPV GKFFQYDTWK | |
| 121 | QSTQRLRRGL PALLRARRGH VLAKELEAFR EAKRHRPLIA LPTQDPAHGG APPEMASNRK (SEQ ID NO: 6) | |
| 1 | MVSPDPQIIV VAPETELASM QVQRTEDGVT IIQIFWVGRK GELLRRTPVS SAMQTPMGIP | |
| 61 | MGKSMLVLLT FLAFASCCIA AYRPSETLCG GELVDTLQFV CGDRGFYFSR PASRVSRRSR | |
| 121 | GIVEECCFRS CDLALLETYC ATPAKSERDV STPPTVLPDN FPRYPVGKFF QYDTWKQSTQ | |
| 181 | RLRRGLPALL RARRGHVLAK ELEAFREAKR HRPLIALPTQ DPAHGGAPPE MASNRK (SEQ ID NO: 7) | |
| 1 | MKSGSGGGSP TSLWGLLFLS AALSLWPTSG EICGPGIDIR NDYQQLKRLE NCTVIEGYLH | |
| 61 | ILLISKAEDY RSYRFPKLTV ITEYLLLFRV AGLESLGDLF PNLTVIRGWK LFYNYALVIF | |
| 121 | EMTNLKDIGL YNLRNITRGA IRIEKNADLC YLSTVDWSLI LDAVSNNYIV GNKPPKECGD | |
| 181 | LCPGTMEEKP MCEKTTINNE YNYRCWTTNR CQKMCPSTCG KRACTENNEC CHPECLGSCS | |
| 241 | APDNDTACVA CRHYYAGVC VPACPPNTYR FEGWRCVDRD FCANILSAES SDSEGFVIHD | |
| 301 | GECMQECPSG FIRNGSQSMY CIPCEGPCPK VCEEEKKTKT IDSVTSAQML QGCTIFKGNL | |
| 361 | LINIRRGNNI ASELENFMGL IEVVTGYVKI RHSHALVSLS FLKNLRLILG EEQLEGNYSF | |
| 421 | YVLDNQNLQQ LWDWDHRNLT IKAGKMYFAF NPKLCVSEIY RMEEVIGTKG RQSKGDINTR | |
| 481 | NNGERASCES DVLHFTSTTT SKNRIIITWH RYRPPDYRDL ISFTVYYKEA PFKNVTEYDG | |
| 541 | QDACGSNSWN MVDVDLPPNK DVEPGILLHG LKPWTQYAVY VKAVILTMVE NDHIRGAKSE | |

```
                           SEQUENCES

601    ILYIRTNASV PSIPLDVLSA SNSSSQLIVK WNPPSLPNGN LSYYIVRWQR QPQDGYLYRH
 661    NYCSKDKIPI RKYADGTIDI EEVTENPKTE VCGGEKGPCC ACPKTEAEKQ AEKEEAEYRK
 721    VFENFLHNSI FVPRPERKRR DVMQVANTTM SSRSRNTTAA DTYNITDPEE LETEYPFFES
 781    RVDNKERTVI SNLRPFTLYR IDIHSCNHEA EKLGCSASNF VFARTMPAEG ADDIPGPVTW
 841    EPRPENSIFL KWPEPENPNG LILMYEIKYG SQVEDQRECV SRQEYRKYGG AKLNRLNPGN
 901    YTARIQATSL SGNGSWTDPV FFYVQAKTGY ENFIHLIIAL PVAVLLIVGG LVIMLYVFHR
 961    KRNNSRLGNG VLYASVNPEY FSAADVYVPD EWEVAREKIT MSRELGQGSF GMVYEGVAKG
1021    VVKDEPETRV AIKTVNEAAS MRERIEFLNE ASVMKEFNCH HVVRLLGVVS QGQPTLVIME
1081    LMTRGDLKSY LRSLRPEMEN NPVLAPPSLS KMIQMAGEIA DGMAYLNANK FVHRDLAARN
1141    CMVAEDFTVK IGDFGMTRDI YETDYYRKGG KGLLPVRWMS PESLKDGVFT TYSDVWSFGV
1201    VLWEIATLAE QPYQGLSNEQ VLRFVMEGGL LDKPDNCPDM LFELMRMCWQ YNPKMRPSFL
1261    EIISSIKEEM EPGFREVSFY YSEENKLPEP EELDLEPENM ESVPLDPSAS SSSLPLPDRH
1321    SGHKAENGPG PGVLVLRASF DERQPYAHMN GGRKNERALP LPQSSTC
        (SEQ ID NO: 8)
```

It is understood that the foregoing detailed description and examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of treating cardiac stem cells comprising:
   a. contacting a population of cardiac stem cells with an effective amount of IGF-1 or a variant thereof; and
   b. contacting the population of cardiac stem cells from step (a) with an effective amount of IGF-2 or a variant thereof,
   wherein the population of cardiac stem cells is isolated from a myocardial tissue of a human subject.

2. The method of claim 1, wherein at least a subset of the population of cardiac stem cells express IGF-1 receptor.

3. The method of claim 1, wherein the effective amount of IGF-1 or a variant thereof is sufficient to increase proliferation of the cardiac stem cells by at least about 10%, as compared to cardiac stem cells in the absence of IGF-1.

4. The method of claim 1, wherein the effective amount of IGF-1 or a variant thereof is about 100 ng/mL.

5. The method of claim 1, wherein the cardiac stem cells are contacted with IGF-1 for at least about 12 hours.

6. The method of claim 1, wherein the effective amount of IGF-2 is sufficient to increase expression of at least one marker for myocyte differentiation by at least about 10%, as compared to cardiac stem cells in the absence of IGF-2.

7. The method of claim 6, wherein the marker for myocyte differentiation is selected from the group consisting of: α-sarcomeric actin, connexin-43, Nkx2.5, GATA-4 and MEF2C.

8. The method of claim 1, wherein the effective amount of IGF-2 or a variant thereof is about 100 ng/mL.

9. The method of claim 1, wherein the cardiac stem cells are contacted with IGF-2 for an amount of time sufficient to increase myocyte formation, as compared to cardiac stem cells in the absence of IGF-2.

10. The method of claim 1, wherein the cardiac stem cells are contacted with IGF-2 for an amount of time sufficient for the cardiac stem cells to confer acquisition of at least one adult cardiomyocyte phenotype, as compared to cardiac stem cells in the absence of IGF-2.

11. The method of claim 10, wherein the adult cardiomyocyte phenotype is selected from the group consisting of: a myocyte volume greater than 2000 μm$^3$, contractility in response to electric stimulation, an elongated morphology, calcium tolerance, expression of at least one contractile protein, and activation of ion current channels.

12. The method of claim 11, wherein the contractile protein is selected from the group consisting of: α-sarcomeric actin, myosin heavy chains, myosin light chains and tropomyosin.

13. The method of claim 1, wherein the population of cardiac stem cells is administered to an area of a damaged heart tissue of the subject in need thereof.

14. The method of claim 1, wherein the subject in need thereof has a damaged myocardium.

15. The method of claim 1, wherein the subject in need thereof is diagnosed with or suffering from a myocardial infarction.

16. The method of claim 1, wherein the subject in need thereof is diagnosed with or suffering from a heart failure.

17. The method of claim 1, wherein the subject in need thereof is diagnosed with or suffering from an age-related cardiomyopathy.

18. The method of claim 11, wherein the adult cardiomyocyte phenotype is a myocyte volume greater than 2000 μm$^3$.

19. The method of claim 11, wherein the adult cardiomyocyte phenotype is contractility in response to electric stimulation.

20. The method of claim 11, wherein the adult cardiomyocyte phenotype is an elongated morphology.

21. The method of claim 11, wherein the adult cardiomyocyte phenotype is calcium tolerance.

22. The method of claim 11, wherein the adult cardiomyocyte phenotype is expression of at least one contractile protein.

23. The method of claim 11, wherein the adult cardiomyocyte phenotype is activation of ion current channels.

24. The method of claim 12, wherein the contractile protein is α-sarcomeric actin.

25. The method of claim 12, wherein the contractile protein is myosin heavy chain.

26. The method of claim 12, wherein the contractile protein is myosin light chain.

27. The method of claim 12, wherein the contractile protein is tropomyosin.

28. The method of claim 1, wherein the cardiac stem cells express at least one of an IGF-1 receptor, (IGF-1R), an IGF-2 receptor (IGF-2R), and an angiotensin type 1 receptor (AT1R), and combinations thereof.

29. The method of claim 1, wherein the cardiac stem cells are lineage negative.

30. The method of claim 1, wherein the cardiac stem cells express c-kit.

31. The method of claim 1, wherein the cardiac stem cells are lineage negative and express c-kit.

32. The method of claim 1, wherein the population of cardiac stem cells is pre-selected for expression of IGF-1R.

33. The method of claim 1, wherein the population of cardiac stem cells is pre-selected for expression of IGF-2R.

34. The method of claim 1, wherein the population of cardiac stem cells is pre-selected for expression of IGF-1R and IGF-2R.

* * * * *

```
                      SEQUENCE LISTING

<160> NUMBER OF SEQ ID NOS: 8

<210> SEQ ID NO 1
<211> LENGTH: 158
<212> TYPE: PRT
<213> ORGANISM: Homo sapiens

<400> SEQUENCE: 1

Met Gly Lys Ile Ser Ser Leu Pro Thr Gln Leu Phe Lys Cys Cys Phe
 1               5                  10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Ser Thr Phe Glu Glu Arg Lys
145                 150                 155

<210> SEQ ID NO 2
<211> LENGTH: 137
<212> TYPE: PRT
```

<213> ORGANISM: Homo sapiens

<400> SEQUENCE: 2

Met Ile Thr Pro Thr Val Lys Met His Thr Met Ser Ser His Leu
1               5                   10                  15

Phe Tyr Leu Ala Leu Cys Leu Leu Thr Phe Thr Ser Ser Ala Thr Ala
                20                  25                  30

Gly Pro Glu Thr Leu Cys Gly Ala Glu Leu Val Asp Ala Leu Gln Phe
            35                  40                  45

Val Cys Gly Asp Arg Gly Phe Tyr Phe Asn Lys Pro Thr Gly Tyr Gly
50                  55                  60

Ser Ser Ser Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
            100                 105                 110

Met Pro Lys Thr Gln Lys Glu Val His Leu Lys Asn Ala Ser Arg Gly
        115                 120                 125

Ser Ala Gly Asn Lys Asn Tyr Arg Met
    130                 135

<210> SEQ ID NO 3
<211> LENGTH: 195
<212> TYPE: PRT
<213> ORGANISM: Homo sapiens

<400> SEQUENCE: 3

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys
                165                 170                 175

Glu Gln Arg Arg Glu Ile Gly Ser Arg Asn Ala Glu Cys Arg Gly Lys
            180                 185                 190

Lys Gly Lys
    195

-continued

```
<210> SEQ ID NO 4
<211> LENGTH: 153
<212> TYPE: PRT
<213> ORGANISM: Homo sapiens

<400> SEQUENCE: 4

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 5
<211> LENGTH: 180
<212> TYPE: PRT
<213> ORGANISM: Homo sapiens

<400> SEQUENCE: 5

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
```

```
                180

<210> SEQ ID NO 6
<211> LENGTH: 180
<212> TYPE: PRT
<213> ORGANISM: Homo sapiens

<400> SEQUENCE: 6

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 7
<211> LENGTH: 236
<212> TYPE: PRT
<213> ORGANISM: Homo sapiens

<400> SEQUENCE: 7

Met Val Ser Pro Asp Pro Gln Ile Ile Val Ala Pro Glu Thr Glu
1               5                   10                  15

Leu Ala Ser Met Gln Val Gln Arg Thr Glu Asp Gly Val Thr Ile Ile
            20                  25                  30

Gln Ile Phe Trp Val Gly Arg Lys Gly Glu Leu Leu Arg Arg Thr Pro
        35                  40                  45

Val Ser Ser Ala Met Gln Thr Pro Met Gly Ile Pro Met Gly Lys Ser
    50                  55                  60

Met Leu Val Leu Leu Thr Phe Leu Ala Phe Ala Ser Cys Cys Ile Ala
65                  70                  75                  80

Ala Tyr Arg Pro Ser Glu Thr Leu Cys Gly Gly Glu Leu Val Asp Thr
                85                  90                  95

Leu Gln Phe Val Cys Gly Asp Arg Gly Phe Tyr Phe Ser Arg Pro Ala
            100                 105                 110

Ser Arg Val Ser Arg Arg Ser Arg Gly Ile Val Glu Glu Cys Cys Phe
        115                 120                 125

Arg Ser Cys Asp Leu Ala Leu Leu Glu Thr Tyr Cys Ala Thr Pro Ala
```

-continued

```
            130                 135                 140
Lys Ser Glu Arg Asp Val Ser Thr Pro Pro Thr Val Leu Pro Asp Asn
145                 150                 155                 160

Phe Pro Arg Tyr Pro Val Gly Lys Phe Phe Gln Tyr Asp Thr Trp Lys
                165                 170                 175

Gln Ser Thr Gln Arg Leu Arg Arg Gly Leu Pro Ala Leu Leu Arg Ala
            180                 185                 190

Arg Arg Gly His Val Leu Ala Lys Glu Leu Glu Ala Phe Arg Glu Ala
        195                 200                 205

Lys Arg His Arg Pro Leu Ile Ala Leu Pro Thr Gln Asp Pro Ala His
    210                 215                 220

Gly Gly Ala Pro Pro Glu Met Ala Ser Asn Arg Lys
225                 230                 235
```

<210> SEQ ID NO 8
<211> LENGTH: 1367
<212> TYPE: PRT
<213> ORGANISM: Homo sapiens

<400> SEQUENCE: 8

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270
```

-continued

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
        290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys

-continued

```
            690                 695                 700
Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
                740                 745                 750

Arg Ser Arg Asn Thr Thr Ala Ala Asp Thr Tyr Asn Ile Thr Asp Pro
                755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
                835                 840                 845

Phe Leu Lys Trp Pro Glu Pro Glu Asn Pro Asn Gly Leu Ile Leu Met
                850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
                915                 920                 925

Gly Tyr Glu Asn Phe Ile His Leu Ile Ile Ala Leu Pro Val Ala Val
                930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
                980                 985                 990

Glu Val Ala Arg Glu Lys Ile Thr Met Ser Arg Glu Leu Gly Gln Gly
                995                 1000                1005

Ser Phe Gly Met Val Tyr Glu Gly Val Ala Lys Gly Val Val Lys
                1010                1015                1020

Asp Glu Pro Glu Thr Arg Val Ala Ile Lys Thr Val Asn Glu Ala
                1025                1030                1035

Ala Ser Met Arg Glu Arg Ile Glu Phe Leu Asn Glu Ala Ser Val
                1040                1045                1050

Met Lys Glu Phe Asn Cys His His Val Val Arg Leu Leu Gly Val
                1055                1060                1065

Val Ser Gln Gly Gln Pro Thr Leu Val Ile Met Glu Leu Met Thr
                1070                1075                1080

Arg Gly Asp Leu Lys Ser Tyr Leu Arg Ser Leu Arg Pro Glu Met
                1085                1090                1095

Glu Asn Asn Pro Val Leu Ala Pro Pro Ser Leu Ser Lys Met Ile
                1100                1105                1110
```

-continued

```
Gln Met Ala Gly Glu Ile Ala Asp Gly Met Ala Tyr Leu Asn Ala
    1115            1120                1125

Asn Lys Phe Val His Arg Asp Leu Ala Ala Arg Asn Cys Met Val
    1130            1135                1140

Ala Glu Asp Phe Thr Val Lys Ile Gly Asp Phe Gly Met Thr Arg
    1145            1150                1155

Asp Ile Tyr Glu Thr Asp Tyr Tyr Arg Lys Gly Gly Lys Gly Leu
    1160            1165                1170

Leu Pro Val Arg Trp Met Ser Pro Glu Ser Leu Lys Asp Gly Val
    1175            1180                1185

Phe Thr Thr Tyr Ser Asp Val Trp Ser Phe Gly Val Val Leu Trp
    1190            1195                1200

Glu Ile Ala Thr Leu Ala Glu Gln Pro Tyr Gln Gly Leu Ser Asn
    1205            1210                1215

Glu Gln Val Leu Arg Phe Val Met Glu Gly Gly Leu Leu Asp Lys
    1220            1225                1230

Pro Asp Asn Cys Pro Asp Met Leu Phe Glu Leu Met Arg Met Cys
    1235            1240                1245

Trp Gln Tyr Asn Pro Lys Met Arg Pro Ser Phe Leu Glu Ile Ile
    1250            1255                1260

Ser Ser Ile Lys Glu Glu Met Glu Pro Gly Phe Arg Glu Val Ser
    1265            1270                1275

Phe Tyr Tyr Ser Glu Glu Asn Lys Leu Pro Glu Pro Glu Glu Leu
    1280            1285                1290

Asp Leu Glu Pro Glu Asn Met Glu Ser Val Pro Leu Asp Pro Ser
    1295            1300                1305

Ala Ser Ser Ser Ser Leu Pro Leu Pro Asp Arg His Ser Gly His
    1310            1315                1320

Lys Ala Glu Asn Gly Pro Gly Pro Gly Val Leu Val Leu Arg Ala
    1325            1330                1335

Ser Phe Asp Glu Arg Gln Pro Tyr Ala His Met Asn Gly Gly Arg
    1340            1345                1350

Lys Asn Glu Arg Ala Leu Pro Leu Pro Gln Ser Ser Thr Cys
    1355            1360                1365
```